US006541002B1

(12) United States Patent
Pomerantz et al.

(10) Patent No.: US 6,541,002 B1
(45) Date of Patent: Apr. 1, 2003

(54) COMPOSITIONS AND METHODS FOR PROVIDING A PROTEIN TO A VIRION

(75) Inventors: Roger J. Pomerantz, Chalfont, PA (US); Mohamad BouHamdan, Lindenwold, NJ (US); Ling-Xun Duan, North Wales, PA (US); YanNing Xue, Beijing (CN)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/281,495

(22) Filed: Mar. 30, 1999

Related U.S. Application Data

(60) Provisional application No. 60/079,822, filed on Mar. 30, 1998.

(51) Int. Cl.$^7$ .................................. A61K 39/00

(52) U.S. Cl. ...................... 424/185.1; 435/5; 435/7.1; 436/501; 530/300

(58) Field of Search .................... 435/5, 7.1; 436/501; 530/300, 350; 424/185.1

(56) References Cited

U.S. PATENT DOCUMENTS 5,622,839 A 4/1997 Moore et al.
5,719,054 A 2/1998 Boursnell et al.

OTHER PUBLICATIONS

Adachi et al., 1986, J. Virol. 59:284–291.
Agostini et al., 1996, J. Mol. Biol. 261:599–606.
Balliet et al., 1994, Virology 200:623–631.
Bartel et al., 1993, Biotech. 14:920–924.
Bolton et al., 1988, Gene 67:31–40.
Bouhamdan et al., 1996, J. Virol. 70:697–704.
Bouyac et al., 1997, J. Virol. 71:9358–9365.
Chardin et al., 1993, Science 260:1338–1343.
Cohen et al., 1990, J. Virol. 64:3097–3099.
Cohen et al., 1990, J. Acquir. Immune Defic. Syndr. 3:11–18.
Connor et al., 1995, Virology 206:935–944.
Cornetta et al., 1993, Hum. Gene Ther. 4:579–588.
Cullen, 1992. Microbiol. Rev. 56:375–394.
de Rocquigny et al., 1997, J. Biol. Chem., J. Biol. Chem. 272:30753–30759.
Debouck, 1992, AIDS Res. Hum. Retrovir. 8:153–164.
Duan et al., 1995, Hum. Gene Ther. 6:1561–1573.
Fletcher et al., 1997, EMBO J. 16:5123–5138.
Guan et al., 1991, Anal. Biochem. 192:262–267.
He et al., 1995, J. Virol. 69:6705–6711.
Heinzinger et al., 1994, Proc. Natl. Acad. Sci. USA 91:7311–7315.
Jones et al., 1990, J. Virol. 64:2265–2279.
Jowett et al., 1995, J. Virol. 69:6304–6313.
Kimpton et al., 1992, J. Virol. 66:2232–2239.
Klotman, 1985, The Kidney 18:1–4.
Kondo et al., 1996, J. Virol. 70:159–164.
Gomez–Lagunas, 1997, FEBS Letters 400:197–200.
Lavallee et al., 1993, J. Acq. Immu. Def. Syndr. 6:529–530.
Lavallee et al., 1994, J. Virol. 68:1926–1934.
Levy et al., 1994, Proc. Natl. Acad. Sci. USA 91:10873–10877.
Levy et al., 1995, J. Virol. 69:1243–1252.
Levy et al., 1993, Cell 72:541–550.
Levy–Mintz et al., 1996, J. Virol. 70:8821–8832.
Liu et al., 1997, J. Virol. 71:7704–7710.
Lu et al., 1993, J. Virol. 67:6542–6550.
Lu et al., 1995, J. Virol. 69:6873–6879.
Mansky, 1996, Virology 222:391–400.
McGeoch et al., 1988, J. Gen. Virol., 69:1531–1574.
Miller et al., 1996, AIDS Res. Hum. Retrovir. 12:859–865.
Miller and Rosman, 1989, BioTechniques 7:980–982.
Mol et al., 1995, Cell 80:869–878.
Olsen et al., 1989, EMBO J. 8:3121–3125.
Paxton et al., 1993, J. Virol. 67:7229–7237.
Pels et al., 1989, JAMA 262:1221–1224.
Percival et al., 1989, J. of Bio. Chem. 264:2593–2598.
Re et al., 1995, J. Virol. 69:6859–6864.
Refaeli et al., 1995, Proc. Natl. Acad. Sci. USA 92:3621–3625.
Richman, 1995, Clin. Infect. Dis. 21(Suppl. 2):S166–S169.
Ridky and Leis, 1995, J. Biol. Chem. 270:29621–29623.
Rogel et al., 1995, J. Virol. 69:882–888.
Rothman and Wieland, 1996, Science 272:227–234.
Salmons and Gunzburg, 1993, Hum. Gene Ther. 4:129–141.
Selig et al., 1997, J. Virol. 71:4842–4846.
Slupphaug et al., 1995, Biochemistry 34:128–138.
Stewart et al., 1997, J. Virol. 71:5579–5592.
Tristem et al., 1992, EMBO J. 11:3405–3412.
Turelli et al., 1997, J. Virol. 71:4522–4530.
Varshney et al., 1988, J. of Vio. Chem. 263:7776–7784.
Wang et al., 1995, J. Biol. Chem. 270:25564–25569.
Wang et al., 1994, Virology 200:524–534.
Weldon et al., 1990, J. Virol. 64:4169–4179.
Westervelt et al., 1992, J. Virol. 66:3925–3931.
Withers–Ward et al., 1997, J. Virol. 71:9732–9742.
Wong–Staal et al., 1987, AIDS Res. Hum. Retrovir. 3:33–39.
Worrad and Caradonna, 1988, J. Virol. 62:4774–4777.
Wu et al., 1995, J. Virol. 69:3389–3398.
Wu et al., 1996, Virology 219:307–313.
Wu et al., 1997, EMBO J. 16:5113–5122.

*Primary Examiner*—James Housel
*Assistant Examiner*—Ulrike Winkler
(74) *Attorney, Agent, or Firm*—Akin Gump Strauss Hauer & Feld, L.L.P.

(57) ABSTRACT

Compositions and methods for rendering a polypeptide capable of binding with Vpr and to susceptible to incorporation into a are provided. Methods of treating a human patient infected with a virus which expresses Vpr and methods of providing a polypeptide to a cell of a human patient are also included. The invention further includes a method of determining whether a polypeptide comprises a Vpr-binding region.

2 Claims, 12 Drawing Sheets

Fig. 4

| | |
|---|---|
| Gln - Pro - Trp - Trp - Ala - Phe - Phe | SEQ ID NO: 3 |
| Thr - Pro - Trp - Trp - Ser - Phe - Met | SEQ ID NO: 4 |
| Thr - Pro - Trp - Trp - Ser - Phe - Met | SEQ ID NO: 4 |
| Ser - Trp - Trp - Ser - Phe - Tyr - Pro | SEQ ID NO: 5 |
| Ser - Trp - Trp - Ser - Phe - Tyr - Pro | SEQ ID NO: 5 |
| Ser - Trp - Trp - Ser- Phe - Ser - Met | SEQ ID NO: 6 |
| Ala - Trp - Trp - Glu - Phe - Leu - Asp | SEQ ID NO: 7 |
| Ala - Trp - Trp - Glu - Phe - Leu - Asp | SEQ ID NO: 7 |
| Lys - Trp - Trp - Glu - Phe - Pro - Ala | SEQ ID NO: 8 |
| Thr - Trp - Trp - His - Phe - Pro - Ala | SEQ ID NO: 9 |

Fig. 5

| | |
|---|---|
| Gln - Asn - Trp - Trp - Phe - Ser - Phe | SEQ ID NO: 10 |
| Thr - Thr - Trp - Trp - Trp - Gln - Phe | SEQ ID NO: 11 |
| Ser - Ala - Pro - Trp - Trp - Thr - Phe | SEQ ID NO: 12 |
| Leu - Pro - Pro - Trp - Ala - Ala - Phe | SEQ ID NO: 13 |
| Gly - His - Thr - Trp - Trp - Thr - Phe | SEQ ID NO: 14 |
| Lys - Pro - Met - Trp - Trp - His - Phe | SEQ ID NO: 15 |
| Ser - Trp - Trp - Ser - Phe - Thr - Pro | SEQ ID NO: 16 |
| Trp - His - Ser - Phe - Pro - Pro - Pro | SEQ ID NO: 17 |
| Trp - His - Ser - Phe - Pro - Asp - Ser | SEQ ID NO: 18 |
| Trp - His - Asp - Phe - Pro - Leu - Val | SEQ ID NO: 19 |
| Gly - Trp - Tyr - Ala - Phe - Thr - Gln | SEQ ID NO: 20 |
| Ser - Trp - Trp - Asp - Phe - Gln - Asn | SEQ ID NO: 21 |
| Trp - His - Thr - Phe - Asp - Tyr - Ser | SEQ ID NO: 22 |
| Lys - Pro - Lys - Trp - Ala - Ile - Val | SEQ ID NO: 23 |
| Thr - Pro - Thr - Leu - Glu - Ala - Ala | SEQ ID NO: 24 |
| Ser - Pro - Leu - Asn - Thr - Gln - Arg | SEQ ID NO: 25 |
| Thr - His - Leu - Ser - Phe - Leu - Ser | SEQ ID NO: 26 |
| Tyr - His - Ser - Phe - Asn - Gly - Thr | SEQ ID NO: 27 |
| Ser - Pro - Pro - Ser - Ala - Met - Leu | SEQ ID NO: 28 |
| Trp - His - Asp - Trp - Ala - Tyr - Trp | SEQ ID NO: 29 |
| Trp - His - Asp - Trp - Ala - Tyr - Trp | SEQ ID NO: 29 |
| Trp - His - Asp - Trp - Ala - Tyr - Trp | SEQ ID NO: 29 |

|  |  | -Histidine |
|---|---|---|
| Gal4 AD | Pep 1 | + |
| Gal4 AD | Pep 2 | − |
| Gal4 AD | Pep 3 | +++ |
| Gal4 AD | Pep 4 | ++ |
| Gal4 AD | Pep 5 | ++ |
| Gal4BD-Vpr + Gal4 AD | Pep 6 | +++ |
| Gal4 AD | Pep 7 | +++ |
| Gal4 AD | Pep 8 | +\− |
| Gal4 AD | Pep 9 | +++ |
| Gal4 AD | Pep 10 | +\− |
| Gal4 AD |  | − |

Flig. 12B

COMPOSITIONS AND METHODS FOR PROVIDING A PROTEIN TO A VIRION

CROSS REFERENCE TO RELATED APPLICATIONS

This application is entitled to priority pursuant to 35 U.S.C. §119(e) to U.S. provisional patent application No. 60/079,822, which was filed on Mar. 30, 1998.

STATEMENT REGARDING FEDERALLY SUPPORTED RESEARCH AND DEVELOPMENT

This research was supported in part by U.S. Government funds (USPHS grants numbers CA47486, AI38666, and AI36557), and the U.S. Government may therefore have certain rights in the invention.

FIELD OF THE INVENTION

The invention relates to antiviral and virucidal compositions and methods and to methods of incorporating a polypeptide into a virus or a virus vector.

BACKGROUND OF THE INVENTION

Human immunodeficiency virus type 1 (HIV-1), a lentivirus, exhibits a complex viral life cycle. Replication of HIV-1 is tightly regulated by numerous cell-and virus-encoded regulatory proteins (Cullen, 1992. Microbiol. Rev. 56:375–394). Essential virus-encoded enzymes, including reverse transcriptase (RT), ribonuclease H (RNaseH), protease (PR), and integrase (IN), do not have cell-encoded counterparts, and for this reason have been used as targets for developing agents which inhibit virus replication without significantly adversely affecting cells (Debouck, 1992, AIDS Res. Hum. Retrovir. 8:153–164; Ridky et al., 1995, J. Biol. Chem. 270:29621–29623; Miller et al., 1996, AIDS Res. Hum. Retrovir. 12:859–865). Although considerable advances have been made in developing agents effective for inhibiting RT and PR, the mutability of HIV-1 has led to strains of the virus which exhibit resistance to such agents (Richman, 1995, Clin. Infect. Dis. 21 (Suppl. 2):S166–S169). Thus, there is a pressing need to develop alternative anti-HIV therapeutic strategies.

Specific cell compartmental localization of therapeutic moieties influences their therapeutic effect. For example, single chain variable region antibody fragments (SFvs) which bind specifically to HIV-1 IN and which are localized in the cytoplasm of a T lymphocyte inhibit infection of the lymphocyte more efficaciously than SFvs which are concentrated in the nucleus of the lymphocyte (Levy-Mintz et al., 1996, J. Virol. 70:8821–8832). Ribozymes have been localized within the virion of murine leukemia virus (MuLV; Rothman et al., 1996, Science 272:227–234). Incorporation of chimeric proteins into retrovirus particles has been reported, wherein the chimeric proteins had amino acid sequences which comprised a portion of the amino acid sequence of a non-viral protein and a portion of either HIV-1 Gag protein or HIV-1 Vpr protein (Wu et al., 1995, J. Virol. 69:3389–3398; Wu et al., 1996, Virology 219:307–313; Jones et al., 1990, J. Virol. 64:2265–2279; Wang et al., 1994, Virology 200:524–534; Weldon et al., 1990, J. Virol. 64:4169–4179).

It has been suggested that sorting of most cellular proteins into specific compartments is determined by protein-protein interactions mediated by specific domains of the proteins involved (Rothman et al., supra). This model of protein sorting is designated the protein-docking model. For example, interaction between a domain of a membrane protein with the signal sequence domain of a cytoplasmic protein can result in export of the cytoplasmic protein into either the Golgi apparatus or a mitochondrion (Rothman et al., supra).

Numerous proteins are packaged into HIV-1 virions, including RT, RNaseH, PR, IN, and proteins designated Gag, Pol, and Env. The genome of HIV-1 encodes other proteins which are packaged into HIV-1 virions, including a protein designated Vpr, which is present in virions of all primate lentivirus (Tristem et al., 1992, EMBO J. 11:3405–3412). The role of Vpr in infection of cells by lentiviruses has been studied extensively. Vpr is expressed relatively late in the lentiviral life cycle and encodes a 14 kilodalton protein which is predominantly localized in the nucleus of an infected cell (Wong-Staal et al., 1987, AIDS Res. Hum. Retrovir. 3:33–39; Lu et al., 1993, J. Virol. 67:6542–6550). Vpr is reported to be incorporated into lentivirus particles in quantities equal to the quantity of Gag protein (Lu et al., Id.; Cohen et al., 1990, J. Virol. 64:3097–3099).

Prior art investigations indicate that the carboxyl terminal domain (p6 region) of the Gag precursor designated p55 is involved in packaging of Vpr into HIV-1 virions (Lavallee et al., 1994, J. Virol. 68:1926–1934; Kondo et al., 1996, J. Virol. 70:159–164; Lu et al., 1995, J. Virol. 69:6873–6879; Paxton et al., 1993, J. Virol. 67:7229–7237). None of these reports identified a site at which p55 and Vpr interact within the amino acid sequence of either Vpr or the p6 region. A direct interaction between Vpr and the nucleocapsid protein designated Ncp7 has been demonstrated (Lim Tung et al., 1997, FEBS Lett. 401:197–201; De Rocquigny et al., 1997, J. Biol. Chem., J. Biol. Chem. 272:30753–30759). This interaction is mediated in vitro by the zinc finger regions of Ncp7 and the sixteen carboxyl terminal amino acids of Vpr (De Rocquigny et al., Id.). It may be that binding of Ncp7 in cooperation with another HIV-1 protein, possibly the p6 region of Gag, induces incorporation of Vpr into mature HIV-1 particles (De Rocquigny et al., Id.).

Several biological functions of Vpr have been defined. For example, Vpr is able to transactivate several heterologous viral promoters which do not share a common DNA sequence element (Cohen et al., 1990, J. Acquir. Immune Defic. Syndr. 3:11–18). Vpr is essential for optimal infection of macrophages by HIV-1 and influences nuclear transport of the HIV-1 pre-integration complex (Balliet et al., 1994, Virology 200:623–631; Connor et al., 1995, Virology 206:935–944; Westervelt et al., 1992, J. Virol. 66:3925–3931; Heinzinger et al., 1994, Proc. Natl. Acad. Sci. USA 91:7311–7315). Vpr also activates transcription from the HIV-1 long terminal repeat (LTR), and influences terminal differentiation of certain cell-types, such as rhabdomyosarcoma cells (Agostini et al., 1996, J. Mol. Biol. 261:599–606; Cohen et al., 1990, J. Acquir. Immune Defic. Syndr. 3:11–18; Wang et al., 1995, J. Biol. Chem. 270:25564–25569; Levy et al., 1993, Cell 72:541–550). Addition of exogenous Vpr to cells latently infected with HIV-1 can reactivate replication of the virus, indicating that Vpr may increase HIV-1 expression by affecting transcriptional or translational events (Levy et al., 1994, Proc. Natl. Acad. Sci. USA 91:10873–10877; Levy et al., 1995, J. Virol. 69:1243–1252). Vpr also causes cell cycle arrest in the G2/M phase and is capable of inducing apoptosis following cell cycle arrest (He et al., 1995, J. Virol. 69:6705–6711; Jowett et al., 1995, J. Virol. 69:6304–6313; Re et al., 1995, J. Virol. 69:6859–6864; Rogel et al., 1995, J. Virol.

69:882–888; Stewart et al., 1997, J. Virol. 71:5579–5592). All of these effects are probably mediated by interactions between Vpr and one or more cellular proteins.

Vpr is able to associate with the major uracil DNA glycosylase (UDG) involved in cellular DNA repair (Slupphaug et al., 1995, Biochemistry 34:128–138; Bou-Hamdan et al., 1996, J. Virol. 70:697–704). The cellular physiological role of UDGs and deoxyuracil triphosphate pyrophosphatases (dUTPases) is believed to be prevention of misincorporation of deoxyuracil into DNA during DNA synthesis. A recent report excludes involvement of UDG in contributing to G2 arrest of cells. Mutational analysis of Vpr has been used to demonstrate that binding of Vpr to UDG is neither necessary nor sufficient to effect cell cycle arrest (Selig et al., 1997, J. Virol. 71:4842–4846). It may be that association of Vpr with UDG permits incorporation of UDG into HIV-1 virions, with the result that, upon subsequent infection of a cell by such a virion, uracil mis-incorporation into DNA transcribed from HIV-1 RNA is reduced. Thus, UDG encoded by a host cell genome may have a physiological role in the infectious cycle of HIV-1 that is similar to the role of dUTPases of non-primate lentiviruses. It has been reported that a strain of caprine arthritis encephalitis virus which is deficient in dUTPase accumulates G-to-A substitutions in its genome in vivo (Turelli et al., 1997, J. Virol. 71:4522–4530). It has also been reported that the vpr gene partially accounts for the lower-than-predicted in vivo mutation rate of HIV-1 (Mansky, 1996, Virology 222:391–400).

The ability of Vpr to associate with other cellular proteins, including glucocorticoid receptors, the basal transcription factor TFIIB, transcription factor Sp1, and the cellular DNA repair protein designated HH23A has been reported (Refaeli et al., 1995, Proc. Natl. Acad. Sci. USA 92:3621–3625; Agostini et al., 1996, J. Mol. Biol. 261:599–606; Wang et al., 1995, J. Biol. Chem. 270:25564–25569; Withers-Ward et al., 1997, J. Virol. 71:9732–9742). It has also been reported that the portion of Vpr that interacts specifically with TFIIB is located between or including amino acid residues 15 and 77 of Vpr (Agostini et al., 1996, J. Mol. Biol. 261:599–606), and that the amino terminal domain of TFIIB is involved in this interaction. At least a portion of the region of HH23A comprising the forty-five carboxyl terminal amino acids of that protein interacts with Vpr. Despite identification of several proteins which specifically interact with Vpr, the mechanism(s) which mediate such interactions are not understood.

It has been suggested that virions derived from a retrovirus such as HIV-1 may be useful as vectors for delivery of a nucleic acid to cells of an animal such as a human (Miller et al., 1989, BioTechniques 7:980–982; Cometta et al., 1993, Hum. Gene Ther. 4:579–588; Salmons et al., 1993, Hum. Gene Ther. 4:129–141). A significant difficulty in designing retrovirus-derived vectors relates to packaging a desired protein into a vector virion.

Because the Vpr protein can be packaged into HIV-1 virions in an amount analogous to the amounts of the major HIV-1 structural proteins, it has been suggested that chimeric proteins having an amino acid sequence comprising a portion of Vpr can be incorporated into HIV-1 -derived virions (Lu et al., 1993, J. Virol. 67:6542–6550; Cohen et al., 1990, J. Virol. 64:3097–3099). Incorporation of a chimeric protein into an HIV-1-derived virion has been reported using a chimeric protein having an amino acid sequence comprising a portion of the sequence of a non-HIV protein and a portion of the sequence of Vpr (Wu et al., 1995, J. Virol. 69:3389–3398; Wu et al., 1996, Virology 219:307–313). For example, a chimeric protein having an amino acid sequence comprising a portion of the sequence of chloramphenicol acetyl-transferase (CAT) and a portion of the sequence of Vpr has been incorporated into an HIV-1-derived virion, and the virion-associated CAT chimeric protein retained CAT activity (Id.). Also, for example, chimeric proteins have been made, each having an amino acid sequence comprising a portion of the amino acid sequence of either HIV-1 Vpr or HIV-2 Vpx and a portion of the amino acid of a protein selected from the group consisting of CAT, staphylococcal nuclease (SN), wild type PR, mutated PR, wild type IN, mutated IN, wild type RT, and mutated RT (Wu et al., 1995, J. Virol. 69:3389–3398; Wu et al., 1996, Virology 219:307–313; Liu et al., 1997, J. Virol. 71:7704–7710; Wu et al., 1997, EMBO J. 16:5113–5122).

The situations described above have severe drawbacks. For example, in certain circumstances, chimeric proteins having an amino acid sequence comprising a portion of the amino acid sequence of Vpr and a portion of the amino acid sequence of a protein other than Vpr may not be suitable for use as anti-viral therapeutic agents. Vpr can arrest the cell cycle when it is present in a cell, and can also induce cellular apoptosis. Such chimeric proteins might also reactivate viral replication in a patient harboring a latent retrovirus, and competition between such a chimeric protein and wild-type Vpr may permit viral escape, meaning that the virus can survive drug treatment and continue to replicate in the individual. Furthermore, such fusion proteins may not exhibit the activity normally associated with the non-Vpr protein component of the chimeric protein.

Thus, the methods of the prior art for incorporating a chimeric protein into an HIV-1 virion have several serious limitations. The present invention overcomes these limitations, in that the present invention does not require use of a chimeric protein having an amino acid sequence comprising a portion of the amino acid sequence of Vpr to incorporate a protein into a virion.

SUMMARY OF THE INVENTION

The invention relates to a polypeptide comprising a Vpr-binding region having the amino acid sequence $Xaa_1$-$Xaa_2$-$Xaa_3$-Phe (SEQ ID NO: 30). wherein $Xaa_1$ is selected from the group consisting of Trp and Phe, wherein each of $Xaa_2$ and $Xaa_3$ is any amino acid residue, and wherein the polypeptide does not normally comprise the region. In one aspect, $Xaa_1$ is Trp. In another aspect, $Xaa_2$ is selected from the group consisting of Ala, Trp, His, Phe, and Tyr. In yet another aspect, $Xaa_3$ is selected from the group consisting of Gln, Thr, Ala, His, Ser, Asp, Glu, and Phe. In still another aspect, $Xaa_2$ is selected from the group consisting of Ala, Trp, His, Phe, and Tyr. In another aspect, $Xaa_2$ is Trp.

In one embodiment of the polypeptide of the invention, the polypeptide comprises a plurality of the Vpr-binding regions, wherein for each of the regions, $Xaa_1$ is independently selected from the group consisting of Trp and Phe, and each of $Xaa_2$ and $Xaa_3$ is independently any amino acid residue. In one aspect, a linker region comprising at least about four amino acid residues is interposed between two of the Vpr-binding regions. In another aspect, the linker region has the amino acid sequence Gly-Gly-Gly-Cys (SEQ ID NO: 33).

In still another aspect, the polypeptide has an amino acid sequence comprising the sequence Trp-$aa_2$-$Xaa_3$-Phe-Gly-Gly-Gly-Cys-Trp-$Xaa_5$-$Xaa_6$-Phe (SEQ ID NO: 34), wherein each of $Xaa_2$, $Xaa_3$, $Xaa_5$, and $Xaa_6$ is any amino acid residue.

The invention also relates to an isolated nucleic acid encoding the polypeptide of the invention, and to a cell comprising that isolated nucleic acid.

The invention further relates to a virion comprising an isolated nucleic acid encoding the polypeptide of the invention. In one aspect, the primate lentivirus is selected from the group consisting of a virion of a virus vector and a primate lentivirus, such as HIV-1.

The invention still further relates to the polypeptide of the invention in substantially pure form.

The invention also relates to a polypeptide comprising a Vpr-binding region, wherein the polypeptide does not normally comprise the region, and wherein the region has an amino acid sequence selected from the group consisting of SEQ ID NOs: 3–29. In one aspect the region has an amino acid sequence selected from the group consisting of SEQ ID NOs: 3–22.

The invention still further relates to a method of rendering a polypeptide capable of binding with Vpr and to a polypeptide made by this method. The method comprises altering the polypeptide such that the altered polypeptide comprises a Vpr-binding region having the amino acid sequence $Xaa_1$-$Xaa_2$-$Xaa_3$-Phe (SEQ ID NO: 30), wherein $Xaa_1$ is selected from the group consisting of Trp and Phe, wherein each of $Xaa_2$ and $Xaa_3$ is any amino acid residue, and wherein the polypeptide does not normally comprise the region. When the polypeptide is altered such that it comprises the region, the altered polypeptide is capable of binding with Vpr. In one aspect of this method, the altered polypeptide comprises a plurality of Vpr-binding regions. For each region $Xaa_1$ is independently selected from the group consisting of Trp and Phe, and each of $Xaa_2$ and $Xaa_3$ is independently any amino acid residue. In another aspect, the linker region has the amino acid sequence Gly-Gly-Gly-Cys (SEQ ID NO: 33).

In still another aspect, the polypeptide has an amino acid sequence comprising the sequence Trp-$Xaa_2$-$Xaa_3$-Phe-Gly-Gly-Gly-Cys-Trp-$Xaa_5$-$Xaa_6$-Phe (SEQ ID NO: 34), wherein each of $Xaa_2$, $Xaa_3$, $Xaa_5$, and $Xaa_6$ is any amino acid residue. The polypeptide may, for example, be an antiviral agent, a virucidal agent, a cellular therapeutic polypeptide, or a cellular suppressant polypeptide.

The invention also relates to a method of rendering a polypeptide susceptible to incorporation into a virion of a virus which normally expresses Vpr and to a polypeptide made by this method. This method comprises altering the polypeptide such that the polypeptide comprises a Vpr-binding region having the amino acid sequence $Xaa_1$-$Xaa_2$-$Xaa_3$-Phe (SEQ ID NO: 30), wherein $Xaa_1$ is selected from the group consisting of Trp and Phe, wherein each of $Xaa_2$ and $Xaa_3$ is any amino acid residue, and wherein the polypeptide does not normally comprise the region. When the polypeptide comprises the region, the polypeptide is susceptible to incorporation into the virion. In one aspect, the virus is a virus vector or a primate lentivirus, such as HIV-1.

The invention further relates to a method of generating a virion comprising a portion of a first polypeptide which does not normally comprise a Vpr-binding region. This method comprises a) providing to a cell a nucleic acid which encodes a second polypeptide having an amino acid sequence which comprises the sequence of the portion and the sequence $Xaa_1$-$Xaa_2$-$Xaa_3$-Phe (SEQ ID NO: 30), wherein $Xaa_1$ is selected from the group consisting of Trp and Phe, and wherein each of $Xaa_2$ and $Xaa_3$ is any amino acid residue, b) providing a competent portion of the genome of a virus which normally expresses Vpr to the cell; and c) thereafter incubating the cell under conditions such that the nucleic acid and the competent portion are expressed, whereby the virion comprising the portion of the first polypeptide is generated. In one aspect the portion comprises every amino acid residue of the first polypeptide.

The invention also relates to a method of providing a polypeptide which does not normally comprise a Vpr-binding region to a human cell. This method first comprises generating a virion by a) providing to a cell a nucleic acid which encodes a second polypeptide having an amino acid sequence which comprises the sequence of the portion and the sequence $Xaa_1$-$Xaa_2$-$Xaa_3$-Phe (SEQ ID NO: 30), wherein $Xaa_1$ is selected from the group consisting of Trp and Phe, and wherein each of $Xaa_2$ and $Xaa_3$ is any amino acid residue, b) providing a competent portion of the genome of a virus which normally expresses Vpr to the cell; and c) thereafter incubating the cell under conditions such that the nucleic acid and the competent portion are expressed, whereby the virion comprising the portion of the first polypeptide is generated. This method further comprises contacting the virion with the human cell. The polypeptide is provided to the human cell when the virion enters the human cell.

The invention also relates to a method of inhibiting replication in a cell of a human patient of a virus which normally expresses Vpr. This method comprises providing to the cell a polypeptide comprising a Vpr-binding region, wherein the region has the amino acid sequence $Xaa_1$-$Xaa_2$-$Xaa_3$-Phe (SEQ ID NO: 30), wherein $Xaa_1$ is selected from the group consisting of Trp and Phe, wherein each of $Xaa_2$ and $Xaa_3$ is any amino acid residue, and wherein the polypeptide does not normally comprise the region. Incorporation of the polypeptide into a virion of the virus is detrimental to replication of the virus. In one aspect of this method, the virion is HIV-1.

The invention further relates to a method of determining whether a polypeptide comprises a Vpr-binding region. The method comprises a) contacting a suspension comprising the polypeptide with at least a portion of Vpr connected to a first support, b) separating the first support from the suspension, and c) assessing whether the polypeptide is associated with the first support. If the polypeptide is associated with the first support then the polypeptide comprises a Vpr-binding region. In one aspect of this method, the portion of Vpr is either His-tagged Vpr or a GST-Vpr chimeric protein. When the portion of Vpr is a GST-Vpr chimeric protein, one aspect of the method further comprises contacting the suspension with a second support prior to contacting the suspension with the chimeric protein. The second support has GST attached thereto. In another embodiment of this aspect, each of the first and second supports comprise a glutathione residue and the polypeptide is a chimeric protein having an amino acid sequence identical to that of a portion of a phage coat protein or a random amino acid sequence.

BRIEF DESCRIPTION OF THE DRAWINGS

FIG. 3, comprising

FIG. 4 lists amino acid sequences (SEQ ID NOs: 3–9) obtained from phage which bound to a chimeric protein having an amino acid sequence comprising a portion of the amino acid sequence of Vpr and a portion of the amino acid sequence of GST, as assessed using the methods described herein. Duplicate sequences indicate sequences which were obtained from multiple phage.

FIG. 5 lists amino acid sequences (SEQ ID NOs: 10–29) obtained from phage which bound to His-tagged Vpr, as assessed using the methods described herein. Duplicate sequences indicate sequences which were obtained from multiple phage.

FIG. 10, comprising

FIG. 12, comprising FIGS. 12A, 12B, and 12C, is a trio of diagrams which depict portions of plasmids encoding integrase (IN) fusion proteins. FIG. 12A depicts a portion of plasmid pSLX-CMV-VPR-PR-IN, which encodes Vpr protein fused at its carboxyl terminus to the HIV-1 protease cleavage site (PR) that occurs between RNase H and IN, which, in turn, is fused to the amino terminus of IN. FIG. 12B depicts a portion of plasmid pSLX-CMV-dWF-IN, which encodes dWF peptide (SEQ ID NO: 1) fused at its carboxyl terminus to the amino terminus of IN. FIG. 12C depicts a portion of plasmid pSLX-CMV-dWF-PR-IN, which encodes dWF peptide (SEQ ID NO: 1) fused at its carboxyl terminus to PR, which, in turn, is fused to the amino terminus of IN.

DETAILED DESCRIPTION

Figure 1:
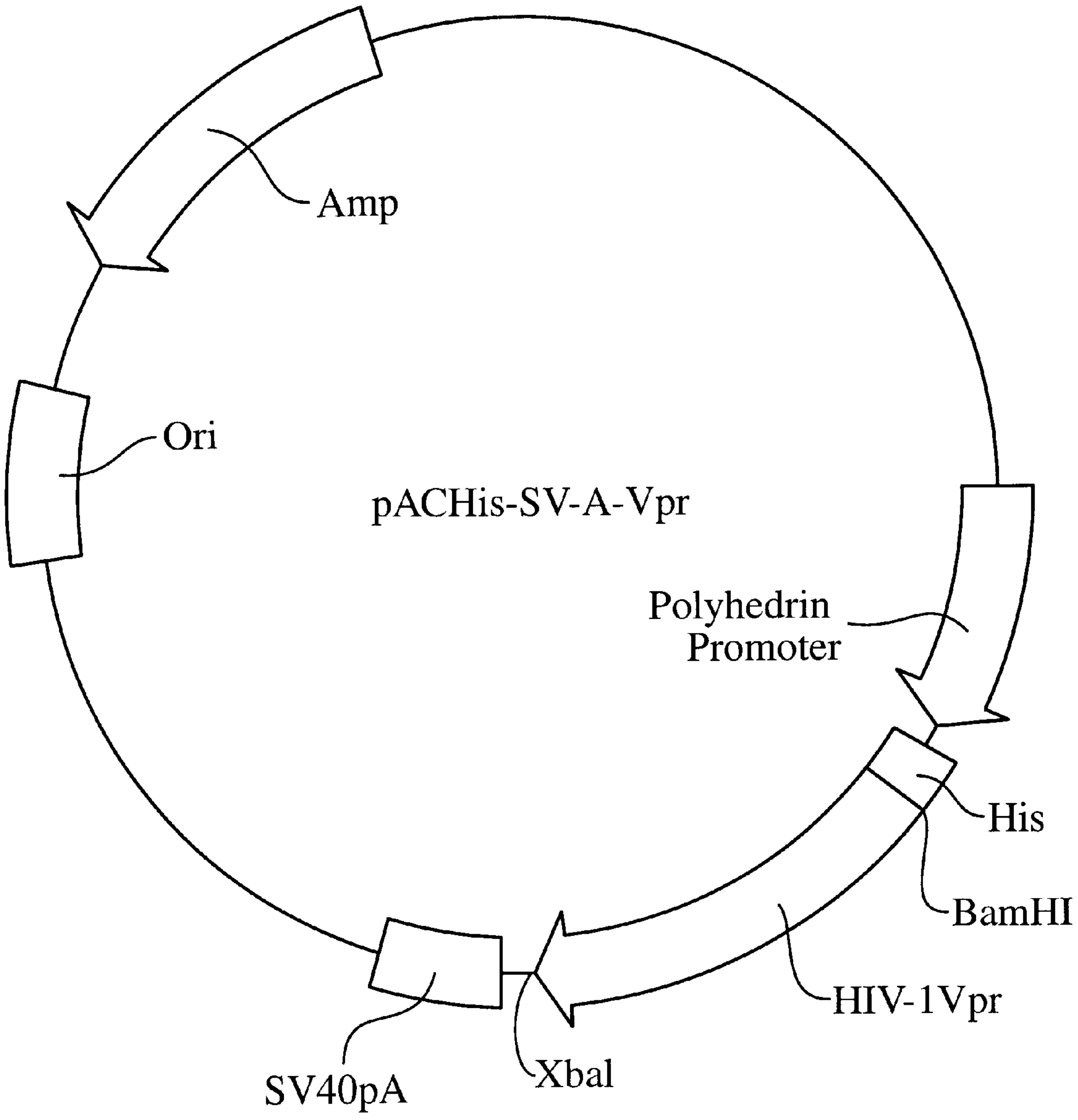
FIG. 1 is a schematic map of the plasmid pACHis-SV-A-Vpr.
Figure 2:
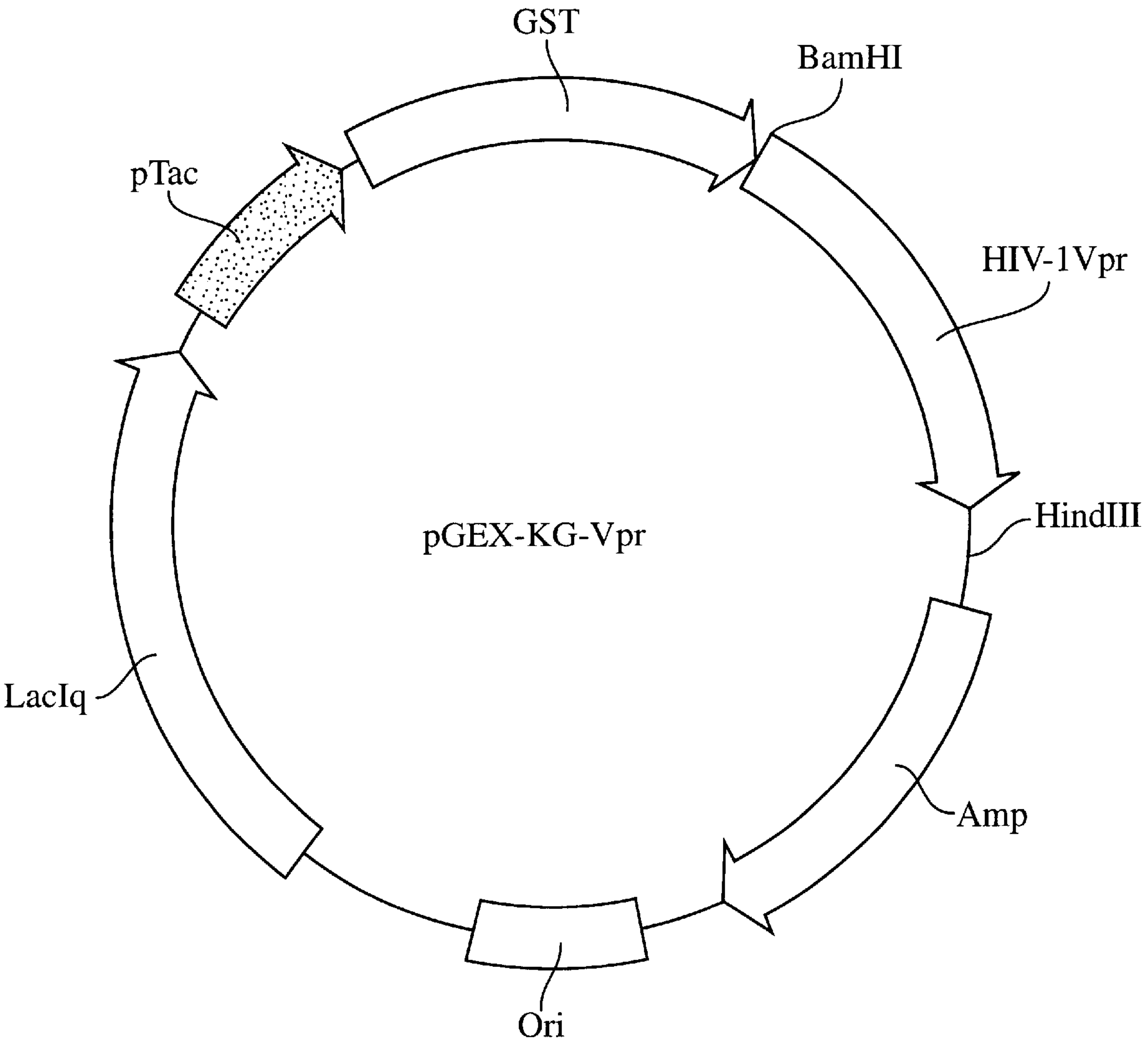
FIG. 2 is a schematic map of the plasmid pGEX-KG-Vpr.

The present invention relates to the discovery that polypeptides having an amino acid sequence comprising $Xaa_1$-$Xaa_2$-$Xaa_3$-Phe (SEQ ID NO: 30), wherein $Xaa_1$ is either Trp or Phe, and wherein each of $Xaa_2$ and $Xaa_3$ is any amino acid residue, are capable of binding with Vpr protein of HIV-1. The present invention includes polypeptides which have an amino acid sequence which do not normally comprise $Xaa_1$-$Xaa_2$-$Xaa_3$-Phe (SEQ ID NO: 30), but which have been modified to have an amino acid comprising this sequence. The present invention also includes methods of making such polypeptides.

The present invention further relates to the further discovery that incorporation of the amino acid sequence, $Xaa_1$-$Xaa_2$-$Xaa_3$-Phe (SEQ ID NO: 30), wherein $Xaa_1$ is either Trp or Phe, and wherein each of $Xaa_2$ and $Xaa_3$ is any amino acid residue, into the amino acid sequence of a polypeptide which does not normally comprise this sequence renders the polypeptide capable of being incorporated into a virion of a virus, such as HIV-1, which expresses Vpr. The present invention therefore includes methods of incorporating such a protein into the virion of a virus, such as HIV-1 or a virus vector derived from HIV-1.

Definitions

As used herein, the following terms have the meanings described herein.

The articles "a" and "an" are used herein to refer to one or to more than one (i.e. to at least one) of the grammatical object of the article. By way of example, "an element" means one element or more than one element.

The term "Vpr-binding region" means a region of a polypeptide, wherein when the polypeptide and Vpr are present in a solvent, the region is capable of specifically interacting with Vpr, whereby the polypeptide forms a complex with Vpr.

A "region" of a polypeptide means a plurality of sequential amino acid residues within the polypeptide. By way of example, a polypeptide having the amino acid sequence Asn-Gln-Gly-Phe-Pro-Thr-Ser has a region having the amino acid sequence Asn-Gln-Gly, a region having the amino acid sequence Gly-Phe-Pro-Thr-Ser, and so forth.

A "portion" of a first polypeptide means a second polypeptide, wherein the amino acid sequence of the first polypeptide comprises the amino acid sequence the second polypeptide. By way of example, a second polypeptide having the amino acid sequence Gly-Phe-Pro-Thr-Ser is a portion of a first polypeptide having the amino acid sequence Asn-Gln-Gly-Phe-Pro-Thr-Ser.

The term "isoform" means an alternate form of an entity which varies at least slightly from a standard form of the entity. For instance, phage particles expressing coat proteins having a random heptapeptide region are isoforms of one another. Similarly, proteins having amino acid sequences which differ by even only a single amino acid residue are isoforms of one another.

The term "antiviral agent" means a composition of matter which, when delivered to a cell, is capable of preventing replication of a virus in the cell, preventing infection of the cell by a virus, or reversing a physiological effect of infection of the cell by a virus.

The term "virucidal agent" means a composition of matter which, when incorporated into a virion of a virus, is capable of preventing replication of the virus in a cell, preventing infection of a cell by the virus, or reversing a physiological effect of infection of a cell by the virus.

The term "cellular therapeutic polypeptide" means a polypeptide which, when delivered to a cell, has a beneficial effect upon the cell.

The term "cellular suppressant polypeptide" means a polypeptide which, when delivered to a cell, inhibits growth of the cell, induces apoptosis, or kills the cell.

The term "competent portion of the genome of a virus" means the portion of the genome of the virus which, when expressed in a cell, results in formation of at least one virion.

The term "chimeric protein" means a protein wherein the amino acid sequence of the protein comprises a portion of the amino acid sequence normally encoded by a gene and at least one amino acid residue not normally encoded by the gene.

A polypeptide "normally" comprises a region if a naturally expressed form of the polypeptide comprises the region.

A polypeptide is "naturally expressed" if the polypeptide is expressed by a naturally occurring organism.

A virus "normally" expresses Vpr protein if a naturally occurring form of the virus comprises either Vpr protein or a gene encoding Vpr protein.

As used herein, the term "substantially pure" describes a compound, such as a protein or polypeptide, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

An "isolated nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

Description

The invention includes the discovery of a consensus amino acid sequence of a Vpr-binding region. If a polypeptide has an amino acid sequence which comprises this consensus sequence, then the polypeptide is capable of binding with Vpr, and if the polypeptide is present in a cell which comprises a competent portion of the genome of a virus which expresses Vpr, then the polypeptide can be incorporated into a virion of the virus. Therefore, the invention also includes a method of incorporating into a virion a polypeptide which does not normally comprise a Vpr-binding region, but which has been altered such that it comprises such a region. Furthermore, if the virion is derived from a virus which is capable of infecting a human cell, then the polypeptide may be delivered to the cell of the human, or to a cell in the human, using the virion.

The consensus amino acid sequence of the Vpr-binding region is $Xaa_1$-$Xaa_2$-$Xaa_3$-Phe (SEQ ID No: 30).

$Xaa_1$ can be either Trp or Phe, and each of $Xaa_2$ and $Xaa_3$ may be any amino acid residue. As described in the Example herein, it was discovered that incorporation of the Trp-Xaa-Xaa-Phe (SEQ ID NO: 31) motif into the amino acid sequence of a polypeptide which does not normally comprise a Vpr-binding region, such as chloramphenicol acetyltransferase (CAT), renders the polypeptide capable of binding with Vpr protein. The polypeptide is thereby furthermore rendered susceptible to incorporation into the virion of a virus which normally expresses Vpr, such as HIV-1. The fact that the Vpr-binding region may also be Phe-Xaa-Xaa-Phe (SEQ ID NO: 32) was realized by analyzing the amino acid sequences of proteins which are known to bind with Vpr, in light of the discovery of the Trp-Xaa-Xaa-Phe (SEQ ID NO: 31) motif.

The polypeptide of the invention therefore comprises a Vpr-binding region having the amino acid sequence $Xaa_1$-$Xaa_2$-$Xaa_3$-Phe (SEQ ID No: 30), wherein the polypeptide does not normally comprise the region. $Xaa_1$ can be either Trp or Phe, and each of $Xaa_2$ and $Xaa_3$ may be any amino acid residue. It has been demonstrated in the Example described herein that when $Xaa_1$ is Trp, $Xaa_2$ may, for example, be selected from the group consisting of Ala, Trp, His, Phe, and Tyr, and $Xaa_3$ may, for example, be selected from the group consisting of Gln, Thr, Ala, His, Ser, Asp, Glu, and Phe. The polypeptide of the invention may have as few as four amino acid residues, namely the Vpr-binding region, or may have numerous amino acid residues in addition to the Vpr-binding region. Thus, for example, the polypeptide of the invention may be a heptapeptide or a chimeric protein which catalyzes a chemical reaction, such as the dWF-CAT protein described herein in the Example.

In a preferred embodiment, the polypeptide of the invention further comprises a second Vpr-binding polypeptide region, wherein the second region has the consensus amino acid sequence of the Vpr-binding region, namely $Xaa_1$-$Xaa_2$-$Xaa_3$-Phe (SEQ ID NO: 30).

As described, $Xaa_1$ can be either Trp or Phe, and each of $Xaa_2$ and $Xaa_3$ may be any amino acid residue. The polypeptide of the invention may further comprise a linker region comprising at least about four amino acid residues and interposed between the two Vpr-binding regions. The linker region may have the amino acid sequence Gly-Gly-Gly-Cys (SEQ ID NO: 33).

Figures 3A, 3B, 3C:
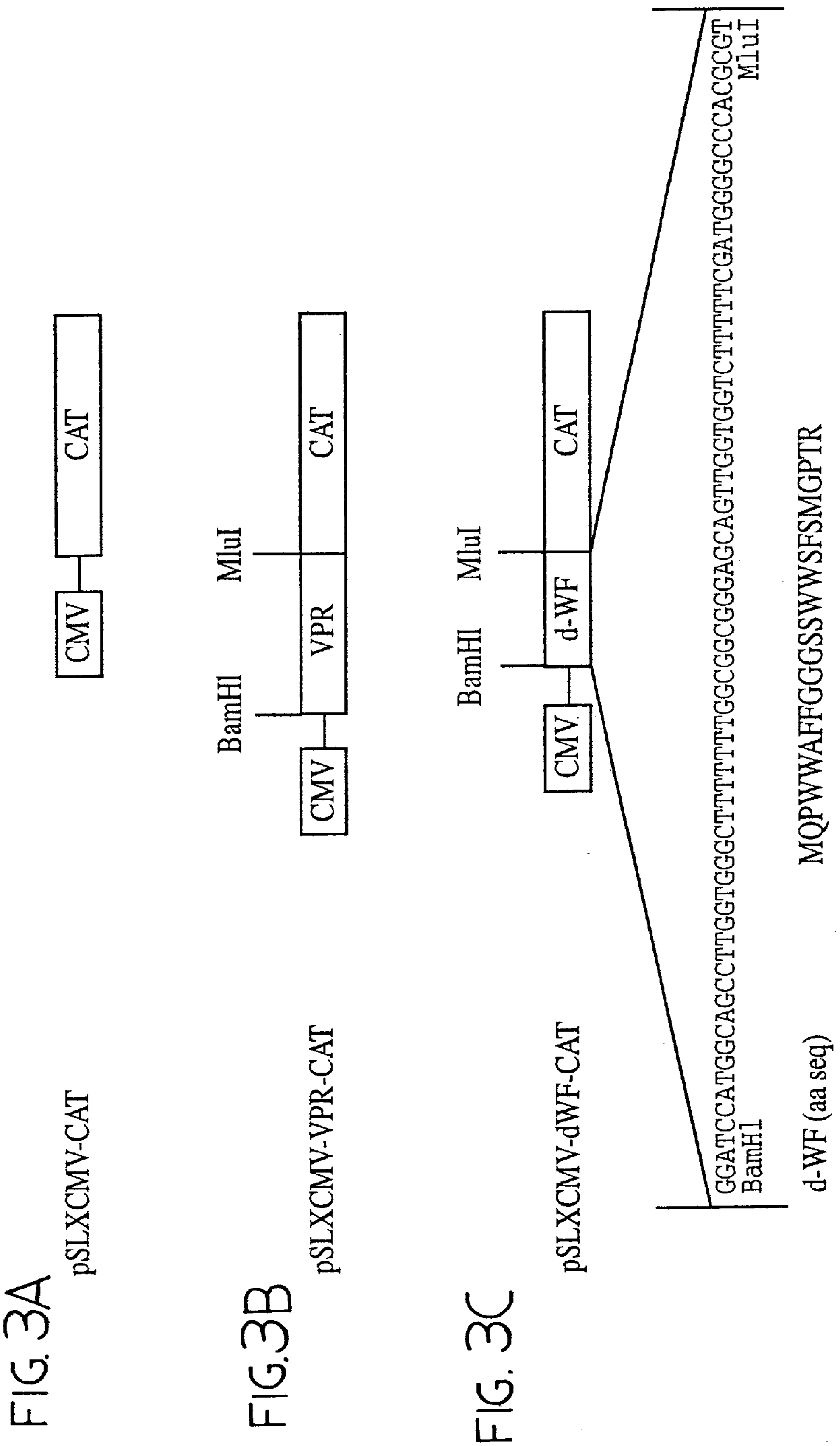
FIGS. 3A, 3B, and 3C is a trio of schematic maps of portions of plasmids. The plasmid depicted in FIG. 3A was used to express CAT. The plasmid depicted in FIG. 3B was used to express a chimeric protein having an amino acid comprising a portion of the amino acid sequence of Vpr and a portion of the amino acid sequence of CAT. The plasmid depicted in FIG. 3C was used to express a chimeric protein having an amino acid comprising a portion of the amino acid sequence of CAT and the amino acid sequence (SEQ ID NO: 1) encoded by the d-WF oligonucleotide (SEQ ID NO: 2).

Thus, the polypeptide of the invention may, for example, have an amino acid sequence comprising the sequence Trp-$Xaa_2$-$Xaa_3$-Phe-Gly-Gly-Gly-Cys-Trp-$Xaa_5$-$Xaa_6$-Phe (SEQ ID NO: 34), wherein each of $Xaa_2$, $Xaa_3$, $Xaa_5$, and $Xaa_6$ is any amino acid residue. Further by way of example, the polypeptide may have an amino acid sequence comprising the sequence listed in FIG. 3, Panel C (SEQ ID NO: 1).

The polypeptide of the invention may comprise any number of Vpr-binding regions having the amino acid sequence $Xaa_1$-$Xaa_2$-$Xaa_3$-Phe (SEQ ID NO: 30).

When the polypeptide of the invention comprises a plurality of Vpr-binding regions, then for each Vpr-binding region, $Xaa_1$ can be either Trp or Phe, independent of the identity of $Xaa_1$ for any other Vpr-binding region of the polypeptide. Similarly for each Vpr-binding region, each of $Xaa_2$ and $Xaa_3$ may independently be any amino acid residue, independent of the identity of $Xaa_2$ and $Xaa_3$ for any other Vpr-binding region of the polypeptide of the invention. A preferred polypeptide comprises two Vpr-binding regions having a linker region interposed between the two regions.

The invention also includes a method of rendering a polypeptide capable of binding with Vpr. This method comprises altering the polypeptide such that the altered polypeptide comprises a Vpr-binding region having the amino acid sequence $Xaa_1$-$Xaa_2$-$Xaa_3$-Phe (SEQ ID No: 30), wherein the polypeptide does not normally comprise the region. $Xaa_1$ can be either Trp or Phe, and each of $Xaa_2$ and $Xaa_3$ may be any amino acid residue. When the altered polypeptide comprises the Vpr-binding region, the altered polypeptide is capable of binding to Vpr. Methods of altering the amino acid sequence of a polypeptide are well known in the art, and are not described herein in depth. The amino acid sequence of a polypeptide can be altered by altering the nucleotide sequence of an oligonucleotide which encodes the polypeptide.

The method used to alter the amino acid sequence of the polypeptide is not critical. What is critical to the compositions and methods of the invention is that the polypeptide of the invention has an amino acid sequence which comprises either the sequence Trp-Xaa-Xaa-Phe (SEQ ID NO: 31) or the sequence Phe-Xaa-Xaa-Phe (SEQ ID NO: 32), wherein Xaa is any amino acid residue. By way of example, the amino acid sequence of the polypeptide may be altered by inserting at least one amino acid residue between two amino acid residues of the polypeptide, by adding at least one amino acid residue to at least one end of the polypeptide, by replacing at least one amino acid residue of the polypeptide with a different amino acid residue, or by deleting at least one amino acid residue of the polypeptide. Further by way of example, if a protein which does not normally comprise a Vpr-binding region comprises a region having the amino acid-Gln-Gly-Gly-Phe-, then the protein may be rendered capable of binding to Vpr by replacing the Gln residue of the protein with a Trp residue or a Phe residue. Methods of performing these amino acid sequence manipulations using one or more oligonucleotides encoding the polypeptide are well known in the art (see, e.g. Sambrook et al., 1989, *Molecular Cloning: A Laboratory Manual*, Cold Spring Harbor Laboratory, New York; Ausubel et al., 1993, *Current Protocols in Molecular Biology*, Green & Wiley, New York).

Methods of expressing proteins encoded by oligonucleotides and methods of protein purification are well known in the art. Preferably, the polypeptide of the invention is substantially pure, as defined herein.

The invention also includes an isolated nucleic acid encoding the polypeptide of the invention, and a cell or a virion comprising such an isolated nucleic acid. The virion may, for example, be a primate lentivirus, such as HIV-1, or a virus vector derived from a primate lentivirus. Methods of incorporating an isolated nucleic acid into a cell or a virion are known in the art.

The polypeptide of the invention is preferably an antiviral agent, a virucidal agent, a cellular therapeutic polypeptide, or a cellular suppressant polypeptide. Antiviral agents are well known and described in the literature. Virucidal agents are also well known and described in the literature.

The invention specifically includes a polypeptide comprising a Vpr-binding region, wherein the polypeptide does not normally comprise the region, and wherein the region has an amino acid sequence selected from the group consisting of SEQ ID NOs: 3–29. Preferably, the region has an amino acid sequence selected from the group consisting of SEQ ID NOs: 3–22.

The invention also includes a method of incorporating a portion of a polypeptide which does not normally comprise a Vpr-binding polypeptide region into a virion. This method comprises providing to a cell a nucleic acid which encodes an amino acid sequence which comprises the sequence of the portion of the polypeptide and a sequence encoding a Vpr-binding region. A competent portion of the genome of a virus which expresses Vpr protein is also provided to the same cell, and a virion comprising the portion of the polypeptide is thereafter generated by incubating the cell under conditions understood in the art. The virus may be, for example, a primate lentivirus such as, for example, HIV-1, or a virus vector.

The invention also includes a method of treating a human patient infected with a virus, such as HIV-1, which expresses Vpr. This method comprises providing to a cell of the patient a polypeptide which is detrimental to replication of the virus and which comprises a Vpr-binding region, wherein said region has an amino acid sequence comprising the sequence $Xaa_1$-$Xaa_2$-$Xaa_3$-Phe (SEQ ID NO: 30).

$Xaa_1$ can be either Trp or Phe, and each of $Xaa_1$ and $Xaa_2$ may be any amino acid residue. When the virus infects the cell, the polypeptide can inhibit replication of the virus and, furthermore, any progeny virions which are generated in the cell comprise the polypeptide. If one of these progeny virions infects another cell, the progeny virion delivers the polypeptide, along with the other virion contents, to a newly-infected cell. Thus, the newly-infected cell is provided with the polypeptide which is detrimental to replication of the virus at the time of infection of the cell. The polypeptide is therefore better able to inhibit replication of the virus in the newly-infected cell than if the polypeptide were provided to the newly-infected cell after the initiation of infection. The polypeptide which is useful in this method may be any polypeptide wherein incorporation of the polypeptide into a virion of the virus is detrimental to replication of the virus. Thus, the polypeptide may be an antiviral agent, a virucidal agent, a cellular suppressant polypeptide, and the like. By detrimentally affecting replication of the virus, further infection of the patient and others to whom the patient might pass the virus is inhibited.

The invention also includes a method of delivering a polypeptide to a cell of a human patient. This method comprises providing to a cell of the patient a virion comprising the polypeptide of the invention. The virion may be a virus vector, such as a replication-deficient HIV-1 virion, for example. Such a virion may be generated in a cell which is provided a competent portion of the genome of the replication deficient form of HIV-1, Vpr protein, and the polypeptide of the invention. The polypeptide may, for example, be an antiviral agent, a virucidal agent, a cellular therapeutic polypeptide, or a cellular suppressant polypeptide, depending upon the desired effect of delivering the polypeptide to the cell. For example, where delivery of a polypeptide to a cancer cell is desired, the polypeptide may be one which induces normal control of growth in the cell or which causes apoptosis of the cell. Similarly by way of example, when the cell is one in which a gene is expressed at an undesirably low level, the polypeptide which is delivered to the cell may be the normal product of the gene, whereby a desirable level of the polypeptide is attained in the cell.

The invention also includes a method of identifying a polypeptide which comprises a Vpr-binding region. This method comprises contacting a suspension comprising the polypeptide with at least a portion of a Vpr protein molecule attached to a first support, separating the first support from the suspension, and determining whether the polypeptide is associated with the first support. The polypeptide may be a known polypeptide, an unknown polypeptide, a mixture of polypeptides, or a library of polypeptides, such as a peptide phage display library. If the polypeptide is associated with the first support, then the polypeptide comprises a Vpr-binding region. As will be understood by one skilled in the art in light of this disclosure, various washing steps may be performed, wherein the first support is contacted with a solution which does not comprise the polypeptide. Any method may be used to determine whether the polypeptide is associated with the first support. For example, proteins, such as antibodies, which specifically bind to the polypeptide may be used to detect the polypeptide on the support using known methods. Further by way of example, the support may be subjected to conditions, such as contact with a solution having a high salt concentration, whereby a protein associated with the support will dissociate from the support. Thereafter, the protein may be detected in the high salt solution.

The portion of Vpr protein which may be used in this method of identifying a polypeptide may, for example, be a His-tagged Vpr protein or a GST-Vpr chimeric protein. Furthermore, the suspension may be contacted with the first support prior to contacting the polypeptide with the portion of Vpr associated with the first support. One reason for doing this would be to reduce the likelihood of mistaking a polypeptide which binds to the first support for a polypeptide which binds to the portion of Vpr. In addition, when the portion of Vpr which is used in this method comprises a chimeric protein molecule, such as GST-Vpr chimeric protein, the suspension may be contacted with a second support having GST attached thereto prior to contacting the suspension with the first support. When GST or GST-Vpr chimeric protein are used, these proteins may be attached to a support comprising a glutathione residue.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

Discovery that the Trp-Xaa-Xaa-Phe (SEQ ID NO: 31) Motif is Involved in Vpr-Protein Interactions A peptide-display phage library was screened to identify individual phage isoforms capable of binding to at least a portion of Vpr. Amino acid sequences of peptides displayed by phage isoforms which were able to bind to Vpr were determined and compared. This comparison revealed a conserved amino acid sequence domain, herein designated "the Trp-Xaa-Xaa-Phe motif" (SEQ ID NO: 31), wherein Xaa is any amino acid residue, which motif was present in twenty-four of the thirty-two phage which bound to Vpr. It was concluded that the Trp-Xaa-Xaa-Phe (SEQ ID NO: 31) directs docking to Vpr of a protein located in the cytosol of an HIV-1-infected cell and having an amino acid sequence comprising the Trp-Xaa-Xaa-Phe (SEQ ID NO: 31) motif. It was further concluded that Trp-Xaa-Xaa-Phe (SEQ ID NO: 31) motif-mediated.docking of a cytosolic protein to Vpr causes the cytosolic protein to be incorporated into an HIV-1 virion.

These conclusions were confirmed by experiments in which chloramphenicol acetyltransferase (CAT) was incorporated into HIV-1 virions after the amino acid sequence of CAT was modified to include the Trp-Xaa-Xaa-Phe (SEQ ID NO: 31) motif. CAT is a protein which does not normally comprise a Vpr-binding region. Two modified forms of CAT were made, one having an amino acid sequence comprising a single Trp-Xaa-Xaa-Phe (SEQ ID NO: 31) motif, and the other having an amino acid sequence comprising a pair of Trp-Xaa-Xaa-Phe (SEQ ID NO: 31) motifs separated by a four amino acid residue linker region. Each of the two modified forms of CAT exhibited the enzymatic activity characteristic of CAT. In addition, each of the two modified forms of CAT was incorporated into HIV-1 virions when the modified form was expressed in a cell which comprised a functional portion of the genome of HIV-1.

The experiments presented in this Example demonstrate a novel strategy for incorporating a compound such as an antiviral agent into a virion.

The materials and methods used in the experiments presented in this Example are now described.

Plasmids

The HIV-1 molecular clones used in this study included $pNL_{4-3}$ and $pNL_{4-3DVpr}$ (Adachi et al., 1986, J. Virol. 59:284–291), which are both plasmids which incorporate a competent portion of the genome of HIV-1. These clones were obtained from the AIDS Reagent Repository of the U.S. National Institutes of Health, and are thus generally available to investigators. $pNL_{4-3DVpr}$ was prepared by deleting a 115 base-pair fragment comprising nucleotides 5621–5736 from the open reading frame of $pNL_{4-3}$ which encodes Vpr.

A retroviral expression vector derived from murine leukemia virus and designated pSLXCMV-CAT has been described and was used in these experiments (Duan et al., 1995, Hum. Gene Ther. 6:1561–1573).

A vector designated pSLXCMV-VPR-CAT was constructed by inserting a 304 base pair BamHI-MluI fragment which comprised the vpr gene and which was obtained from HIV-1 strain NL4–3 between the BamHI and MluI restriction endonuclease sites located in the polylinker region of the pSLXCMV vector. The stop codon of the vpr gene was removed and replaced by a MluI site, to permit fusion of a 677 base pair MluI-BamHI fragment which comprised the cat gene between the MluI and BglII restriction endonuclease sites of pSLXCMV-VPR*. The stop codon was removed by PCR using a specific primer complementary to the 3'-portion of the gene. The cat gene was obtained as described (Duan et al., 1995, Hum. Gene Ther. 6:1561–1573).

A vector designated pSLXCMV-dWF-CAT was constructed by inserting a 76 base pair BamHI-MluI fragment (SEQ ID NO: 2) which encoded the Trp-Xaa-Xaa-Phe dimer (dWF) described herein (SEQ ID NO: 1) between the BamHI and MluI restriction endonuclease sites of pSLXCMV-VPR-CAT.

The 76 base pair BamHI-MluI fragment encoding dWF (SEQ ID NO: 2) was synthesized by the polymerase chain reaction (PCR) by annealing and amplifying the polynucleotides identified herein as WF-dimer-1 (SEQ ID NO: 35) and WF-dimer-2 (SEQ ID NO: 36).

Methods for constructing plasmids pGBT10, which encodes the Gal4 DNA-binding domain (Gal4BD), and pGADGH, which encodes the Gal4 activation domain (Gal4AD), have been described (Chardin et al., 1993, Science 260:1338–1343). Methods for constructing plasmid pGA-Vpr have also been described (BouHamdan et al., 1996, J. Virol. 70:697–704).

The udg gene was amplified by PCR using as a template the cDNA which was designated UDG, as described (BouHamdan et al., 1996, J. Virol. 70:697–704). A 5' primer designated UDG1 (SEQ ID NO: 37) and a 3' primer designated UDG2 (SEQ ID NO: 38) were used to amplify udg. UDG1 comprised an EcoRI endonuclease site at the 5'-end thereof, and UDG2 comprised a SalI endonuclease restriction site at the 3'-end thereof. After treating the amplified udg gene with restriction endonucleases EcoRI and SalI, the amplified gene was cloned in frame into the corresponding restriction endonuclease sites of pGBT10 to yield a plasmid designated pGB-UDG. pGBT10 can be synthesized as described (BouHamdan et al., 1996, J. Virol. 70:697–704). Mutagenesis of the udg gene in pGB-UDG was performed using pairs of mutated complementary PCR primers, as described (Lavallee et al., 1993, J. Acq. Immu. Def. Syndr. 6:529–530). Two rounds of PCR amplification were performed using the pairs of mutated complementary primers designated UDG222 (SEQ ID NOs: 39 and 40), UDG225 (SEQ ID NOs: 41 and 42), and UDG152 (SEQ ID NOs: 43 and 44), to yield plasmids designated pUDGW222G, pUDGF225G and pUDGQ152L, respectively. Each amplified and mutated udg sequence was excised using restriction endonucleases EcoRI and SalI and was ligated into the corresponding restriction endonuclease sites of pGBT10.

DNA fragments encoding the variable heptapeptide region of the coat protein of individual phage isoforms selected from the library described herein were amplified using PCR from purified phage DNA. Amplified peptide-encoding DNA was cloned in frame between the EcoRI and BglII restriction endonuclease sites of pGADGH for use in yeast two-hybrid system experiments.

Purification of His-Tagged Vpr

The baculovirus expression vector designated pACHis-SV-A-Vpr, which is depicted in FIG. 1, was used to generate recombinant Vpr-baculovirus. Vector pACHis-SV-A was prepared by modifying a commercially available pVL1393 based vector (Pharmingen, Inc., California) as follows. An SV40 polyadenylation site (pA) was inserted between the EcoRI and BglII restriction endonuclease sites of pVL1393 and a polynucleotide encoding six histidine residues was inserted downstream of the translation initiation codon of the vector using standard molecular biology techniques to yield pACHisSV-A. The vpr gene of HIV-1 was amplified by performing PCR using $pNL_{4-3}$ and primers designated Vpr-1, which had the nucleotide sequence 5'-CGGATCCATGGAACAAGCCCCAGAAGAC-3' (SEQ ID NO: 45), and Vpr-2, which had the nucleotide sequence 5'-CTATAGACTAGGATCTACTGGATCC-3' (SEQ ID NO: 46), as described (Adachi et al., 1986, J. Virol. 59:284–291). The 304 base pair amplified vpr DNA fragment was digested using restriction endonucleases BamHI and XbaI, and was then inserted between the BamHI and XbaI restriction endonuclease sites of pACHisSV-A to yield pACHis-SV-AVpr.

Baculovirus vectors comprising pACHis-SV-AVpr were generated and purified using the Pharmingen Manufacture Baculoviral Expression System kit, according to the manufacturer's suggested procedure. SF9 cells were cultured as described (Bouyac et al., 1997, J. Virol, 71:9358–9365). SF9 cells in culture were infected with about $1\times10^8$ colony-forming units per milliliter of a baculovirus vector comprising pACHis-SV-AVpr. About 2 liters of SF9 cell culture medium was harvested by centrifugation three days later to pellet cells expressing His-tagged Vpr.

SF9 cell pellets were re-suspended in His-binding buffer, which comprised 20 millimolar Tris buffer, adjusted to pH 7.9 using HCl, 0.5 molar NaCl, and 5 millimolar imidazole at 4 degrees Celsius, and the cell suspension was sonicated to disrupt cells and shear cellular DNA. Cellular debris, which contained most of the Vpr expressed by the cells in an insoluble form, was collected by centrifuging the sonicated cell suspension at 20,000×g for about fifteen minutes, and was washed once with His-binding buffer to yield a washed pellet. The washed pellet was dissolved in a solution comprising His-binding buffer and 6 molar guanidine and was incubated at room temperature (i.e. about 20 degrees Celsius) for about one hour with slow magnetic stirring to suspend pelleted protein. Insoluble material was removed by centrifuging the suspension at 20,000×g for about twenty minutes. The supernatant was mixed with 1 milliliter of His-Bind resin which had been pre-equilibrated with the buffer included therewith (Novagen, Madison, Wis.) and incubated at 4 degrees Celsius for about one hour, during which period the mixture was gently swirled.

Material which did not specifically bind to the resin was removed by washing the resin using a solution comprising His-binding buffer and 6 molar guanidine. The washing procedure comprised repeated cycles of buffer addition, swirling, settling, and decanting. Material which specifically bound to the resin was thereafter eluted by mixing the resin with a solution comprising His-binding buffer, 6 molar guanidine, and 0.5 molar imidazole and separating the resin from the solution. The solution was dialyzed against water, purified His-tagged Vpr precipitated in the dialyzed solution, and precipitated His-tagged Vpr was collected by centrifugation and resuspended in phosphate buffered saline (PBS).

The purity of His-tagged Vpr was assessed by gradient SDS-PAGE using 4–20% (w/v) polyacrylamide gel (Bio-Rad, Inc., Richmond, Calif.). The purity of His-tagged Vpr was also assessed by Western blot analysis of His-tagged Vpr preparations using a rabbit polyclonal antibody preparation comprising antibodies which bound to Vpr or using a mouse monoclonal antibody which specifically bound to Vpr.

GST Chimeric Protein Expression and Purification

The plasmid pGEX-GST-VPR was made by inserting a 304 base pair BamHI-HindIII fragment comprising the vpr gene between the BamHI and HindIII restriction endonuclease sites of plasmid pGEX-KG, as described (Guan et al., 1991, Anal. Biochem. 192:262–267). Expression of a GST-Vpr chimeric protein having an amino acid sequence comprising a portion of the amino acid sequence of GST and a portion of the amino acid sequence of Vpr was performed as described (Smith et al., 1988, Gene 67:31–40). GST-Vpr chimeric protein expression was induced by exposure of cells to 0.1 millimolar IPTG for about one hour. Cells were harvested by centrifugation and suspended in 10 milliliters of PBST, which comprised 20 millimolar phosphate buffer adjusted to pH 7.3, 150 millimolar NaCl, 1% (v/v) Triton X-100, 2 millimolar EDTA, 0.4 millimolar PMSF, 2 milligrams per milliliter leupeptin, 50 milligrams per milliliter TLCK, and 100 milligrams per milliliter TPCK. Cells were lysed by sonication. The lysate was centrifuged at 10,000×g for about 10 minutes at 4 degrees Celsius. The supernatant was applied to a glutathione agarose column (Sigma Chemical Co., St. Louis, Mo.) having a bed volume of 1 milliliter. Prior to applying the supernatant, the glutathione column had been equilibrated with TBST, which comprised 50 millimolar Tris buffer adjusted to pH 7.5 using HCl, 150 millimolar NaCl, and 0.5% (v/v) Tween 20. After washing the column with PBS, the GST-Vpr chimeric protein bound to the column was eluted by applying to the column a solution comprising 5 millimolar glutathione, 50 millimolar Tris buffer adjusted to pH 8.0 using HCl, and 150 millimolar NaCl.

Peptide-Display Phage Library Screening Using GST-Vpr-Glutathione-Agarose.

A commercial peptide-display phage library kit (Ph.D.™ Phage Display Peptide Library Kit, New England Biolabs, Beverly, Mass.) comprised a multiplicity of M13 phages, each of which comprised a coat protein comprising a region of seven amino acid residues having a random sequence. The phage library was panned as follows. 50 milligrams of purified GST was directly applied to a glutathione agarose column having a bed volume of 50 milliliters to yield GST-glutathione-agarose beads. Similarly, 50 milligrams of purified GST-Vpr chimeric protein was directly applied to a glutathione agarose column having a bed volume of 50 milliliters to yield GST-Vpr-glutathione-agarose beads. The column was incubated for about thirty minutes at 4 degrees Celsius, and then the column was washed with about 10 milliliters of TB ST. About $2\times10^{11}$ plaque forming units (pfu) of phage from the phage display kit were suspended in 250 milliliters of TBST, and the suspension was mixed with the glutathione agarose beads to which GST had been bound. The beads and the suspension were incubated for about one hour at room temperature (i.e. about 20 degrees Celsius), and then the mixture was centrifuged at low speed to pellet the beads. The beads in the pellet were washed with 250 milliliters of TBST. Phage which did not bind to glutathione agarose beads were mixed with either glutathione agarose beads to which purified GST had been bound or glutathione agarose beads to which purified GST-Vpr chimeric protein had been bound. Each of these two mixtures was incubated at room temperature for about one hour, and then phage which did not bind to the beads were removed as described herein. Phage which bound to either the GST-glutathione agarose beads or to the GST-Vpr-glutathione agarose beads were eluted from the beads by mixing the beads with 100 milliliters of a solution comprising 5 millimolar reduced glutathione in TBS. TBS comprised 50 millimolar Tris buffer adjusted to pH 7.5 using HCl and 150 millimolar NaCl. The specificity of binding between GST and phage which bound to GST-glutathione-agarose and the specificity of binding between GST-Vpr chimeric protein and phage which bound to GST-Vpr-glutathione-agarose were assessed according to the protocol included with a GST Gene Fusion System Kit (Pharmacia LKB Biotechnology Inc., Piscataway, N.J.).

Peptide-Display Phage Library Screening Using His-Tagged Vpr Protein.

An alternative phage library panning method involved contacting phage with His-tagged Vpr protein which was bound to the surface of a well of a multi-well plate. This method was performed as follows.

Purified denatured His-tagged Vpr protein was suspended in a solution comprising 6 molar guanidine. About 300 microliters of the suspension was added to individual target wells of a twelve-well plate and, thereafter, a twenty-fold volumetric excess of a solution comprising 0.1 molar $NaHCO_3$ at pH 8.9 was added to each well. The plate also comprised control wells which were not coated with His-tagged Vpr protein. Control wells were treated with 6 M guanidine and with the $NaHCO_3$ solution. Each plate was incubated overnight at 4 degrees Celsius prior to use.

About 1 milliliter of a blocking solution comprising 5 milligrams per milliliter bovine serum albumin and 0.1 molar $NaHCO_3$ and having a pH of about 8.9 was added to each well, and the plate was incubated for about thirty minutes at ambient temperature (i.e. about 20 degrees Celsius). The blocking solution was decanted from each well, and each well was washed by adding about 1 milliliter of PBS to the well and thereafter decanting the PBS. This washing step was repeated a total of three times. An aliquot of the phage display peptide library comprising about $2\times10^{11}$ phage suspended in 200 microliters of TBST containing 1 milligram per milliliter BSA was added to each well, and the plate was incubated for about thirty minutes at ambient temperature.

Following incubation with phage, each well was washed by adding about 1 milliliter of TBST to the well and thereafter decanting the TBST. This washing step was repeated ten times in order to remove nonspecifically bound phage from the well. Phage which bound specifically to His-tagged Vpr protein in a target well were eluted by adding a suspension comprising about 100 micrograms of His-tagged Vpr protein in about 1 milliliter to the well and thereafter collecting the suspension according to directions provided by the kit manufacturer. Binding specificity was determined according to directions provided by the kit manufacturer by comparing titer between target wells and control wells.

Selection of Individual Phage Isoforms

Phage library panning methods were repeated to improve the specificity with which phage bound to either GST-Vpr-glutathione-agarose or His-tagged Vpr. A total of three rounds of panning were performed, regardless of which of the two panning methods was used.

Phage which exhibited specific binding to either GST-Vpr-glutathione-agarose or His-tagged Vpr protein were obtained, and were applied to a lawn of *E. coil* cells to permit selection of individual phage isoforms. Phage isoforms obtained from individual plaques were selected for amplification in *E. coli* cells. Phage DNA was subsequently extracted from the cells using known methods and sequenced. Oligonucleotide 96gIII (SEQ ID NO: 44) was used as a sequencing primer, and sequencing was performed using an automated fluorescently-labeled nucleotide sequencer (ABI Model 377 sequencer; Applied Biosystems, Inc., Foster City, Calif.).

Use of a Yeast Two-Hybrid System

The yeast reporter strain, HF7c, which comprises two Gal4-inducible reporter genes, namely HIS3 and LacZ, has been described (BouHamdan et al., 1996, J. Virol. 70:697–704). HF7c cells were transformed with two plasmids, pGB-UDG and pGA-Vpr, using known methods to yield double transformant HF7c cells. These cells were plated on a synthetic medium which did not comprise tryptophan, leucine, or histidine, and the plates were incubated for three days as described (BouHamdan et al., 1996, J. Virol. 70:697–704). Cells obtained from these plates were used in a liquid culture assay with yeast reporter strain SFY526 to detect beta-galactosidase activity, as described (BouHamdan et al., 1996, J. Virol. 70:697–704; Bartel et al., 1993, Biotech. 14:920–924). O-nitrophenyl-beta-D-galactosidase was used as the substrate in the assay, and each assay was performed in triplicate.

Transfection and Culture Conditions 293T cells were cultured in Dulbecco's modified Eagle's medium (DMEM) supplemented with 10% (v/v) fetal calf serum (FCS) at 37 degrees Celsius. Transfection was performed using a standard calcium-phosphate transfection method (Promega Corp, Madison, Wis.).

About $10^6$ 293T cells were grown in dishes having a diameter of 10 centimeters. These cells were co-transfected with 10 micrograms of either plasmid $pNL_{4-3}$ or plasmid $pNL_{4-3DVpr}$, and with 10 micrograms of a plasmid selected from the group consisting of plasmid pSLXCMV-CAT, plasmid pSLXCMV-VPR-CAT, and plasmid pSLXCMV-dWF-CAT. After transfection, the cells were incubated in medium for about seven hours. The medium was then removed and replaced with fresh medium, and cells and medium were collected about forty-eight hours after the medium was replaced. At that time, the medium comprised virus produced by the cells. The amount of virus present in the medium was determined by assessing the amount of HIV-1 p24 antigen in the medium, using a p24 ELISA kit obtained from Dupont (Wilmington, Del.).

CAT Activity Assay

CAT activity assays were performed as described (Refaeli et al., 1995, Proc. Natl. Acad. Sci. USA 92:3621–3625). Briefly, about $10^6$ transfected cells were harvested by centrifugation. Pelleted cells were lysed in 0.9 milliliter of CAT lysis buffer (Promega Corp., Madison, Wis.) to yield a crude extract. 50 microliters of crude extract was used in CAT assays, and the results of the assays were normalized to account for variation in the protein content of the various crude extracts which were made.

Virions obtained from the medium in which transfected 293T cells were grown were concentrated by ultracentrifuging the medium in a Sorval A-621 rotor for about three hours at 20,000 rotations per minute. The pellet obtained following ultracentrifugation was re-suspended and applied to a 20% to 65% (w/v) sucrose solution gradient in a centrifuge tube by centrifuging the tube in a Sorval TH-641 rotor for about sixteen hours at 40,000 rotations per minute and thereafter collecting fractions. The amount of HIV-1 p24 antigen in each fraction was assessed, and fractions containing the greatest amounts of p24 were selected. The concentration of virions in each of the selected fractions was adjusted to normalize p24 antigen concentration among the fractions. Virions in each fraction were lysed by suspending the virions in 0.3 milliliters of CAT lysis buffer (Promega Corp., Madison, Wis.) and incubating the suspension, first at room temperature for about fifteen minutes, and then at 65 degrees Celsius for an additional about fifteen minutes. CAT activity was assessed in lysed virion preparations.

CAT activity was assessed by thin-layer chromatographic separation of $^{14}$C-chloramphenicol from its acetylated derivatives. Radioactivity was quantitated by standard liquid scintillation methods.

Western Blot Analysis

Individual suspensions of yeast cells having approximately equal cell density were lysed in radioimmunoprecipitation assay (RIPA) buffer, as described (BouHamdan et al., 1996, J. Virol. 70:697–704). Immunoprecipitation of cell lysates was performed using a mouse antibody designated Tebu, which is an anti-Gal 4 DNA-binding domain antibody and protein A-Sepharose™ beads. Precipitated proteins were washed with RIPA buffer and were subjected to SDS-PAGE using a 12% (w/v) gel. Following PAGE, proteins in the gel were electrotransferred to a PVDF membrane (Amersham, Arlington Heights, Ill.). The membrane was contacted with a solution comprising the antibody, Tebu, and then was contacted with a solution comprising a swine anti-rabbit immunoglobulin designated Dako, which was covalently linked to horseradish peroxidase. The presence of Dako at discrete locations on the membrane was demonstrated using ECL™ Western blotting detection reagents (Amersham, Arlington Heights, Ill.).

Oligonucleotides

Sequences of certain oligonucleotides described herein are presented in Table 1. Residues indicated in bold type indicate restriction endonuclease sites. Underlined residues differ from wild type sequences in oligonucleotides having point mutations.

TABLE 1

Selected oligonucleotide sequences.

| Identifier | Nucleotide Sequence | SEQ ID NO |
|---|---|---|
| 5' primer UDG1 | 5'-AAA**GAATT**CC CCTCCTCGCC GCTGAGTGCC-3' | 37 |
| 3' primer UDG2 | 5'-CCCATTGACT GGAAGGAGCT GTGA**GTCGAC** TAAATC-3' | 38 |
| Mutated complementary primers UDG225 | 5'-GGCTGGGAGC AGGGCACTGT GCAGTT-3'<br>3'-CCGACCCTCG TCCCGTGACT ACGTCAA-5' | 41<br>42 |
| Mutated complementary primers UDG222 | 5'-GAGCGAGGCG GGGAGCAGTT C-3'<br>3'-CTGGCTCCGC CCCTCGTCAA G-5' | 39<br>40 |
| Mutated complementary primers UDG152 | 5'-CATGGACCTA ATCTAGCTCA CGGGCTC-3'<br>3'-GTACCTGGAT TAGATCGAGT GCCCGAG-5' | 43<br>44 |

TABLE 1-continued

Selected oligonucleotide sequences.

| Identifier | Nucleotide Sequence | SEQ ID NO |
|---|---|---|
| WF-dimer 1 | 5'-C**GGATCC**ATG CAGCCTTGGT GGGCTTTTTT TGGCGGCGGG AGCAGTTGGT GGTCTTTTTC GATGGGGCCC **ACGCGT**-3' | 35 |
| WF-dimer 2 | 5'-**ACGCGT**GGGC CCCATCGAAA AAGACCACCA ACTGCTCCCG CCGC-3' | 36 |
| 96gIII sequencing primer | 5'-CCCTCATAGT TAGCGTAACG-3' | 44 |

The results of the experiments presented in this Example are now described.

Identification of Vpr-Specific Polypeptide Binding Regions

After three rounds of panning using the GST-Vpr-glutathione agarose method described herein, phage isoforms were identified, each of which comprised a heptapeptide region. The amino acid sequences of the heptapeptide regions of the ten phage isoforms which were identified in this manner are listed in FIG. 4. Three pairs of individual phage isoforms each comprised heptapeptide regions having the same amino acid sequence. Thus, this method of panning resulted in identification of seven non-identical amino acid sequences of Vpr-specific polypeptide binding regions.

After three rounds of panning using the His-tagged Vpr method described herein, phage isoforms were identified, each of which comprised a heptapeptide region. The amino acid sequences of the heptapeptide regions of the twenty-two individual phage isoforms which were identified in this manner are listed in FIG. 5. Three of the individual phage isoforms comprised heptapeptide regions having the same amino acid sequence. Thus, this method of panning resulted in identification of twenty non-identical amino acid sequences of Vpr-specific polypeptide binding regions.

Combining the results obtained using the two panning methods, twenty-seven amino acid sequences of Vpr-specific polypeptide binding regions were identified. These sequences are summarized in Table 2.

TABLE 2

Heptapeptide Amino Acid Sequences

| Identifier | Amino Acid Sequence | SEQ ID NO |
|---|---|---|
| | Gln-Pro-Trp-Trp-Ala-Phe-Phe | 3 |
| | Thr-Pro-Trp-Trp-Ser-Phe-Met | 4 |
| | Ser-Trp-Trp-Ser-Phe-Tyr-Pro | 5 |
| | Ser-Trp-Trp-Ser-Phe-Ser-Met | 6 |
| | Ala-Trp-Trp-Glu-Phe-Leu-Asp | 7 |
| | Lys-Trp-Trp-Glu-Phe-Pro-Ala | 8 |
| | Thr-Trp-Trp-His-Phe-Pro-Ala | 9 |
| | Gln-Asn-Trp-Trp-Phe-Ser-Phe | 10 |
| Pep #4 | Thr-Thr-Trp-Trp-Trp-Gln-Phe | 11 |
| Pep #5 | Ser-Ala-Pro-Trp-Trp-Thr-Phe | 12 |
| Pep #6 | Leu-Pro-Pro-Trp-Ala-Ala-Phe | 13 |
| Pep #7 | Gly-His-Thr-Trp-Trp-Thr-Phe | 14 |
| Pep #9 | Lys-Pro-Met-Trp-Trp-His-Phe | 15 |
| Pep #1 | Ser-Trp-Trp-Ser-Phe-Thr-Pro | 16 |
| Pep #8 | Trp-His-Ser-Phe-Pro-Pro-Pro | 17 |
| Pep #10 | Trp-His-Ser-Phe-Pro-Asp-Ser | 18 |
| Pep #3 | Trp-His-Asp-Phe-Pro-Leu-Val | 19 |
| | Gly-Trp-Tyr-Ala-Phe-Thr-Gln | 20 |
| | Ser-Trp-Trp-Asp-Phe-Gln-Asn | 21 |
| | Trp-His-Thr-Phe-Asp-Tyr-Ser | 22 |
| Pep #2 | Lys-Pro-Lys-Trp-Ala-Ile-Val | 23 |
| | Thr-Pro-Thr-Leu-Glu-Ala-Ala | 24 |

TABLE 2-continued

Heptapeptide Amino Acid Sequences

| Identifier | Amino Acid Sequence | SEQ ID NO |
|---|---|---|
| | Ser-Pro-Leu-Asn-Thr-Gln-Arg | 25 |
| | Ser-Pro-Pro-Ser-Ala-Met-Leu | 28 |
| | Thr-His-Leu-Ser-Phe-Leu-Ser | 26 |
| | Tyr-His-Ser-Phe-Asn-Gly-Thr | 27 |
| | Trp-His-Asp-Trp-Ala-Tyr-Trp | 29 |

Twenty of the twenty-seven amino acid sequences listed in Table 2 comprise the amino acid motif, Trp-$Xaa_1$-$Xaa_2$-Phe, wherein $Xaa_1$ and $Xaa_2$ are various amino acid residues. In the amino acid sequences listed in Table 2, $Xaa_1$ was Ala, Trp, His, Phe, or Tyr, and $Xaa_2$ was Gln, Thr, Ala, His, Ser, Asp, Glu, or Phe. $Xaa_1$ was most commonly Trp.

Yeast Two-Hybrid Experiments

Intracellular interaction of ten of the heptapeptide regions listed in Table 2 with HIV-1 Vpr was further tested using the yeast two-hybrid system.

Figure 6:
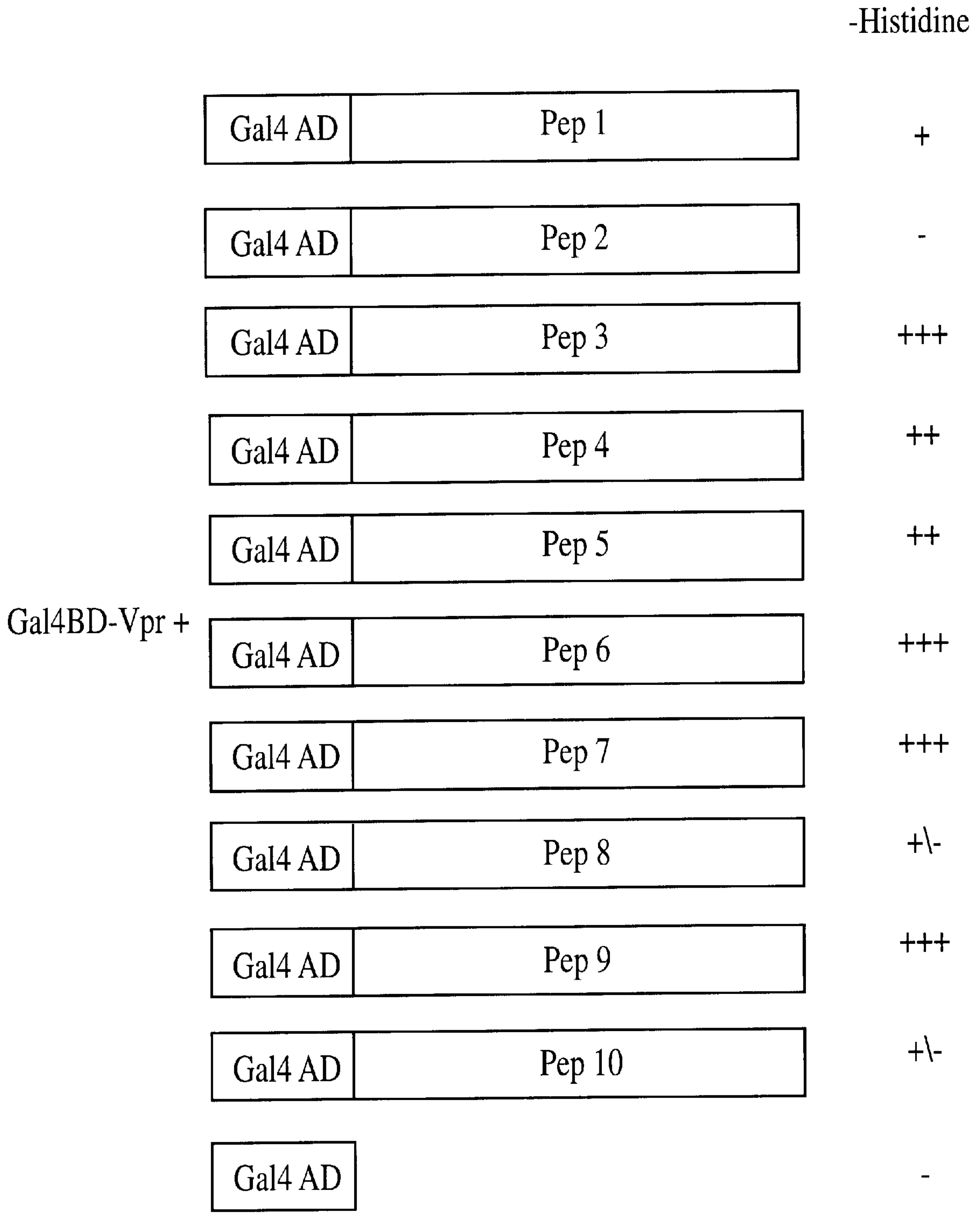
FIG. 6 depicts the ability of HF7c yeast double transformants to grow on histidine-deficient medium. Yeast were transformed with a nucleic acid encoding a chimeric protein having an amino acid comprising a portion of the amino acid sequence of Vpr and a portion of the amino acid sequence of Gal4BD and with a nucleic acid encoding either Gal4AD or a chimeric protein having an amino acid comprising one of the amino acid sequences listed in Table 2 of Example 1 and a portion of the amino acid sequence of Gal4AD. The ability of double transformant yeast is indicated by '+++,' meaning that the double transformant exhibited vigorous growth on the medium, by '++,' meaning that the double transformant exhibited moderate growth on the medium, or by '+' or '+/–,' meaning that the double transformant exhibited little or no growth on the medium.

HF7c cells were transformed with a plasmid having a nucleotide sequence encoding a Vpr-Gal4DB chimeric protein, which had an amino acid sequence comprising a portion of the amino acid sequence of Vpr and a portion of the amino acid sequence of Gal4DB. The same cells were also transformed with a plasmid having a nucleotide sequence encoding a chimeric protein having an amino acid sequence comprising a portion of the amino acid sequence of Gal4AD and one of the amino acid sequences which is associated with an identifier in Table 2 (i.e. one of Pep#1–10; SEQ ID NOs: 10–19). The results of these experiments are shown in FIG. 6.

Double transformant HF7c cells were inoculated onto medium which did not comprise histidine, and the ability of the cells to grow on the medium was assessed. As indicated in FIG. 6, nine double transformants were able to grow on histidine-deficient medium. These results indicate that each chimeric protein of the pair of chimeric proteins expressed in each of these nine double transformants was able to interact with the other chimeric protein of the pair. Double transformants which expressed chimeric proteins having an amino acid sequence identified in Table 2 as Pep#3 (SEQ ID NO: 19), Pep#6 (SEQ ID NO: 13), Pep#7 (SEQ ID NO: 14), or Pep#9 (SEQ ID NO: 15) were better able to grow on histidine-deficient medium than the other double transformants tested. Double transformants which expressed chimeric proteins having an amino acid sequence identified in Table 2 as Pep#4 (SEQ ID NO: 11) or Pep#5 (SEQ ID NO: 12) were better able to grow on histidine-deficient medium than those which expressed chimeric proteins having an amino acid sequence identified in Table 2 as Pep#1 (SEQ ID NO: 16), Pep#8 (SEQ ID NO: 17), or Pep#10 (SEQ ID NO: 18). The presence of the amino acid sequence motif Trp-Xaa-Xaa-Phe (SEQ ID NO: 31), wherein Xaa is any amino acid, in the amino acid sequence of a chimeric protein of each of the double transformants which was able to grow on histidine-deficient medium indicates that this motif represents the sequence of a polypeptide region with which Vpr can specifically interact.

The double transformant which expressed either wild type Gal4AD or a chimeric protein having an amino acid comprising the heptapeptide identified as Pep#2 in Table 2 (SEQ ID NO: 10) was unable to grow on histidine-deficient medium. These observations, coupled with the fact that Pep#2 in Table 2 (SEQ ID NO: 10) is the only one of the ten sequences studied which does not comprise the amino acid sequence motif $Xaa_1$-$Xaa_2$-$Xaa_3$-Phe (SEQ ID NO: 30), wherein $Xaa_1$ is Trp or Phe and each of $Xaa_2$ and $Xaa_3$ is any amino acid residue, provide further evidence that this motif is necessary for interaction between Vpr and another protein.

Interaction between Vpr and UDG Isoforms

High affinity binding of Vpr with UDG and co-immunoprecipitation of Vpr with UDG has been reported (BouHamdan et al., 1996, J. Virol. 70:697–704). However, the mechanism by which the two proteins interact was unknown until the present invention. In light of the discovery of the Trp-Xaa-Xaa-Phe (SEQ ID NO: 31) motif, the amino acid sequence of human UDG was examined. It was discovered that amino acid residues 222–225 of human UDG have the sequence Trp-Glu-Gln-Phe (SEQ ID NO: 45). Furthermore, as indicated in Table 3, the region of UDG having an amino acid sequence comprising the Trp-Xaa-Xaa-Phe (SEQ ID NO: 31) motif is conserved among various organisms.

TABLE 3

Comparison of the amino acid sequences of UDG obtained from various sources.

| UDG | Amino Acid Sequence | SEQ ID NO |
|---|---|---|
| Hum (210–238)[1] | RAHQANSHKERG**W**EQ**F**TDAVVSWLNQNSN | 46 |
| Yea (228–256)[2] | RAHNANSESKHG**W**ET**F**TKRVVQLLIQDRE | 47 |
| Eco (129–157)[3] | RAGQAHSEASLG**W**ET**F**TDKVISLINQHRE | 48 |
| HSV1 (243–271)[4] | KRGAAASESRIG**W**DR**F**VGGVIRRLAARRP | 49 |
| HSV2 (223–251)[5] | KRGAAASTSKLG**W**DR**F**VGGVVRRLAARRP | 50 |
| EBV (155–183)[6] | QKGKPGSEADIG**W**AW**F**TDHVISLLSERLK | 51 |

Numbers in parentheses indicate the amino acid residues depicted in this Table, numbered from the amino terminus of the protein.
Amino acids are identified using standard single letter codes.
The Trp and Phe residues of the Trp-Xaa-Xaa-Phe (SEQ ID NO: 31) motif are aligned and highlighted.
Sources of UDG:
[1]Mol et al., 1995, Cell 80:869–878
[2]Percival et al., 1989, J. Biol. Chem 264: 2593–2598
[3]Varshney et al., 1988, J. Biol. Chem 263: 7776–7784
[4]McGeoch et al., 1988, J. Gen. Virol. 69: 1101–1107
[5]Worrad et al., 1988, J. Virol. 62: 4774–4777
[6]Olsen et al., 1989, EMBO J. 8: 3121–3125

Figure 7:
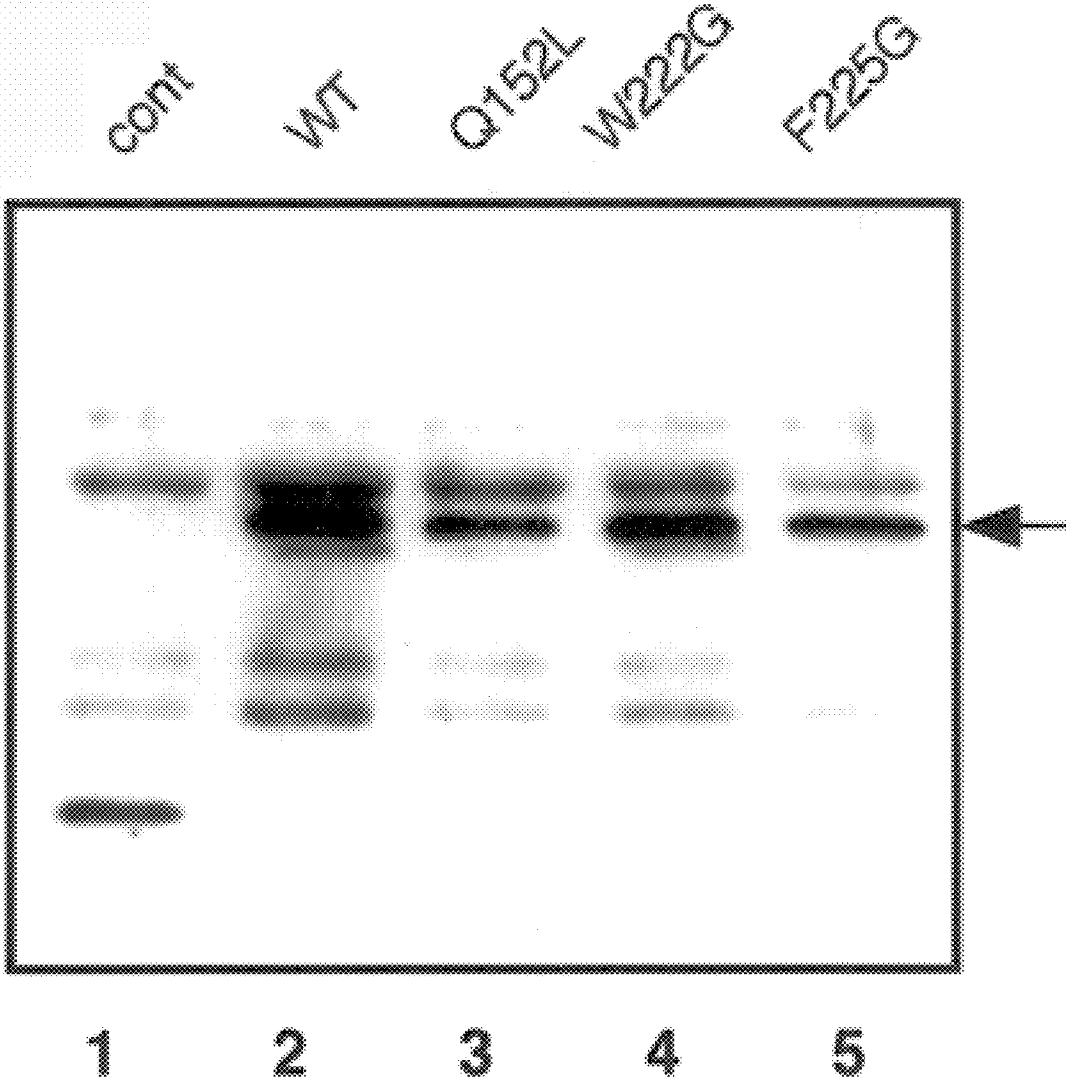
FIG. 7 is an image of a Western blot in which a murine antibody which specifically binds to Gal4BD was bound to chimeric proteins, each of which proteins had an amino acid sequence comprising a portion of the amino acid sequence of Gal4BD and a portion of the amino acid sequence of either wild type (WT; Gal4BD-UDG)) or a mutated (Q152L, W222G, or F225G) UDG protein. Cell extract from cells transfected with vector alone was applied to the lane designated 'cont'. The arrow indicates the approximate position corresponding to Gal4BD-UDG.

In order to test the apparent correlation between the presence of the Trp-Xaa-Xaa-Phe (SEQ ID NO: 31) motif in the amino acid sequence of UDG and the ability of UDG to interact with Vpr, UDG isoforms having single amino acid residue sequence differences relative to wild type UDG were made as described herein. Chimeric UDG-Gal4BD proteins each had an amino acid sequence comprising a portion of the amino acid sequence of Gal4BD and a portion of the amino acid sequence of either wild type UDG or a UDG isoform. Wild type Gal4BD and each of the chimeric UDG-Gal4BD chimeric proteins were separately expressed in HF7c yeast cells by transformation of cells, as described herein. The cells were also transformed with a plasmid having a nucleotide sequence encoding the Vpr-Gal4DB chimeric protein to yield double transformant cells. The presence in the double transformant cells of wild type Gal4BD or a UDG-Gal4BD chimeric protein was confirmed by Western blot analysis using an antibody which specifically binds to Gal4BD, as depicted in FIG. 7. Double transformant cells were inoculated onto histidine-deficient medium, and the ability of the cells to grow on that medium was assessed.

Figure 8:
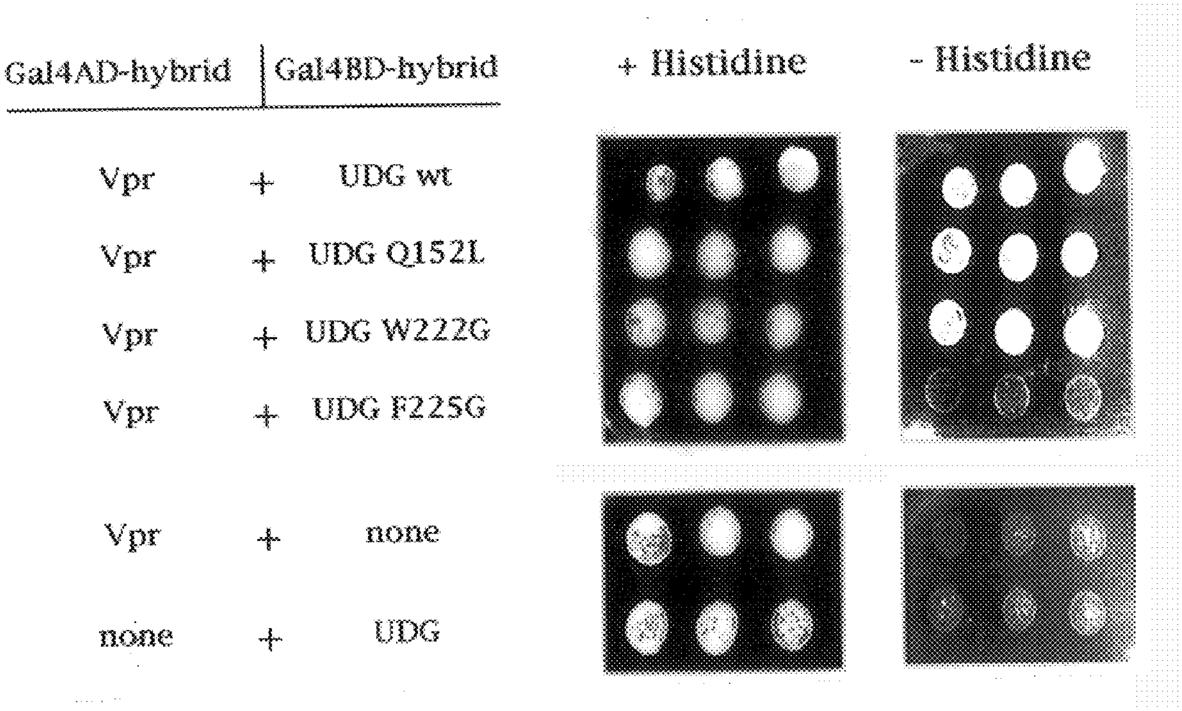
FIG. 8 is an image depicting the growth of double transformant yeast which were patched on medium which contained (left column of images) or which did not contain (right column of images) histidine. Growth in the absence of histidine is an indication of the interaction between the Gal4AD hybrid protein, which had an amino acid sequence comprising either the amino acid sequence of Gal4AD or a portion of the amino acid sequence of Gal4AD and a portion of the amino acid sequence of Vpr, and the Gal4BD hybrid protein, which had an amino acid sequence comprising either the amino acid sequence of Gal4BD or a portion of the amino acid sequence of Gal4BD and a portion of the amino acid sequence of wild type or mutated UDG.

As depicted in FIG. 8, the double transformant designated UDG F225G, in which the Phe residue present at amino acid residue 225 of wild type UDG was replaced with a Gly residue at the corresponding position in the UDG-Gal4BD chimeric protein, was unable to grow on histidine-deficient medium. This observation indicates that this alteration in the Trp-Xaa-Xaa-Phe (SEQ ID NO: 31) motif of UDG renders UDG incapable of interacting with Vpr, meaning that this residue is critical for interaction between UDG and Vpr.

As depicted in FIG. 8, double transformants designated UDG Q152L, in which the Gln residue present at amino acid residue 152 of wild type UDG was replaced with a Leu residue at the corresponding position in the UDG-Gal4BD chimeric protein, and UDG W222G, in which the Trp residue present at amino acid residue 222 of wild type UDG was replaced with a Gly residue at the corresponding position in the UDG-Gal4BD chimeric protein, were able to grow on histidine-deficient medium. Thus, UDG isoforms having these two amino acid sequence alterations retained the ability to interact with Vpr.

Figure 9:
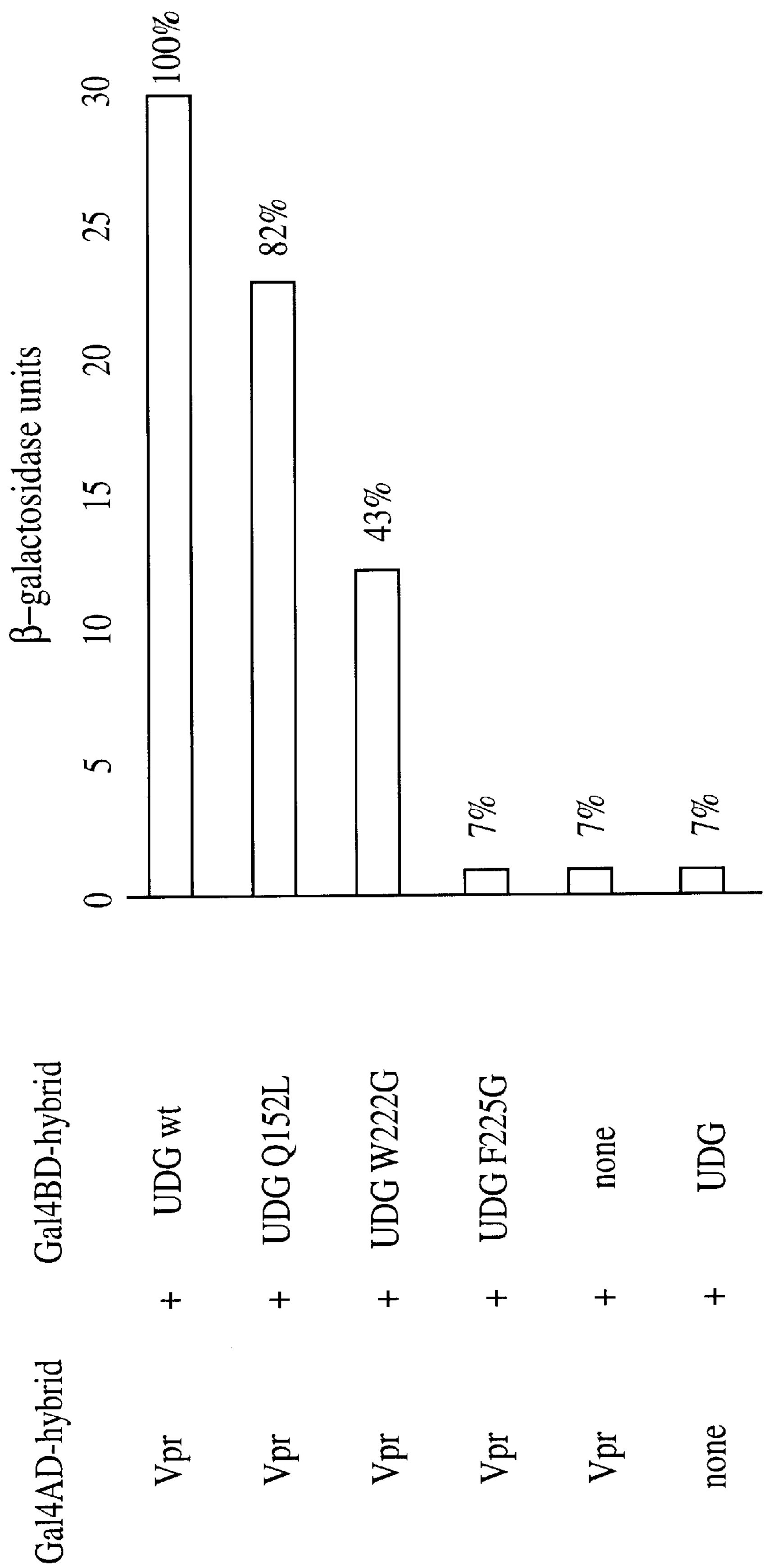
FIG. 9 is a graph depicting the amount of beta-galactosidase activity detected in liquid cultures of double transformant yeast. Values depicted are means of triplicate determinations made using three independent transformants.
Figure 10A:
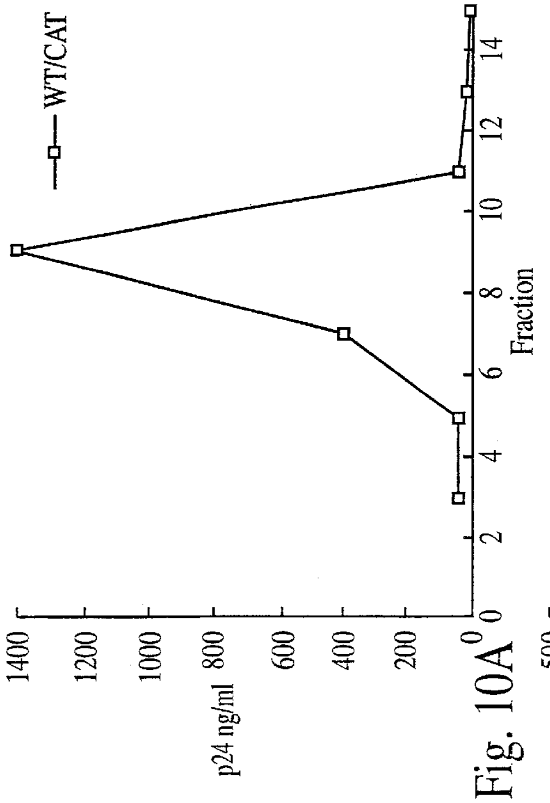
FIGS. 10A, 10B, 10C, and 10D, is a quartet of graphs, each of which depicts the amount of p24 antigen detected in centrifugal sedimentation fractions prepared using HIV-1 virions collected from the culture supernatants of cells designated WT/CAT, WT/Vpr-CAT, WT/WF-CAT, or $Vpr^-$/WF-CAT cells.
Figure 10B:
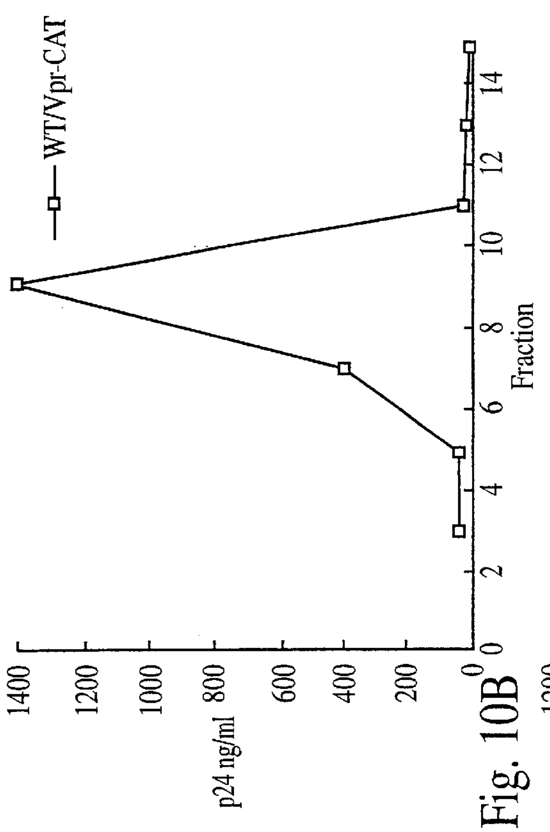
Figure 10C:
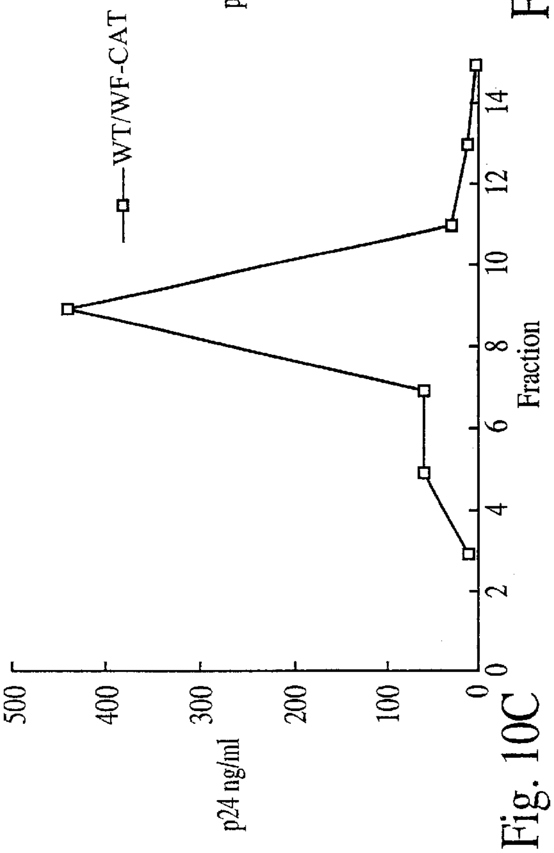
Figure 10D:
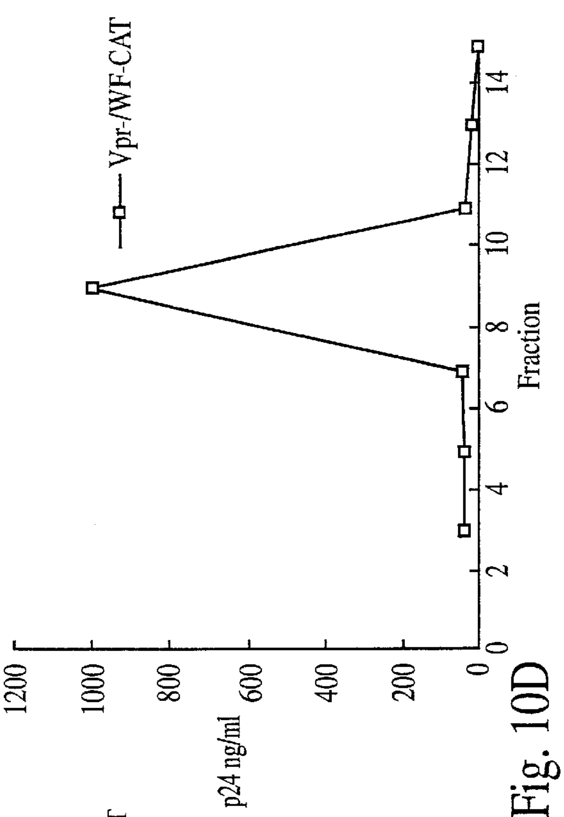

The relative ability of UDG isoforms to interact with Vpr was assessed by quantitative liquid culture beta-galactosidase assay, as described herein. The results of these assays are summarized in FIG. 9. The UDG-Gal4BD chimeric protein expressed by double transformant UDG F225G exhibited only 7% of the ability to interact with Vpr-Gal4AD chimeric protein, relative to the ability of UDG-Gal4BD chimeric protein having an amino acid sequence comprising the wild type UDG sequence. The UDG-Gal4BD chimeric protein expressed by double transformant UDG W222G also exhibited less than half (43%) of the ability to interact with Vpr-Gal4AD chimeric protein, relative to the ability of UDG-Gal4BD chimeric protein having an amino acid sequence comprising the wild type UDG sequence. The UDG-Gal4BD chimeric protein exhibited an ability to interact with Vpr-Gal4AD chimeric protein which was comparable to (i.e. 82% of) the ability of UDG-Gal4BD chimeric protein having an amino acid sequence comprising the wild type UDG sequence to interact with Vpr-Gal4AD chimeric protein. These results clearly indicate that the Trp residue at amino acid position 222 and the Phe residue at amino acid position 225 of UDG are necessary for interaction between UDG and Vpr.

Incorporation of CAT-dWF Chimeric Proteins into HIV-1 Virions.

The inventors believed that the presence in a polypeptide of a region having an amino acid sequence comprising the Trp-Xaa-Xaa-Phe (SEQ ID NO: 31) motif could render the protein capable of interacting with Vpr, and that this interaction could furthermore cause the protein to be incorporated into HIV-1 virions in a cell which comprises a competent portion of the genome of HIV-1. This hypothesis was tested by altering the cat gene as described herein to encode a protein having the amino acid sequence of both CAT and a either one or two copies of the Trp-Xaa-Xaa-Phe (SEQ ID NO: 31) motif.

Incorporation of foreign proteins into HIV-1 particles has been reported by fusion of those proteins with Vpr (Wu et al., 1995, J. Virol. 69:3389–3398; Wu et al., 1996, Virology 219:307–313). These reports demonstrated the capability of Vpr to direct the packaging of foreign proteins, such as CAT, into HIV-1 virions, when the foreign protein and Vpr are co-expressed in the form of a chimeric protein. Therefore, plasmid pSLXCMV-VPR-CAT, which encodes a Vpr-CAT chimeric protein having an amino acid sequence comprising a portion of the amino acid sequence of Vpr and a portion of the amino acid sequence of CAT, was used as a positive control in these experiments.

A dWF-CAT chimeric protein having an amino acid sequence comprising a portion of the amino acid sequence of CAT and two copies of the Trp-Xaa-Xaa-Phe (SEQ ID NO: 31) motif was constructed. The two sequence motifs were separated by a linker amino acid sequence having the sequence Gly-Gly-Gly-Ser (SEQ ID NO: 52) to allow flexibility and proper folding of the polypeptide regions encoded by the motifs.

293T cells were co-transfected with plasmid $pNL_{4\text{-}3}$ or plasmid $pNL_{4\text{-}3DVpr}$ and with plasmid pSLXCMV-CAT, plasmid pSLXCMV-VPR-CAT, or plasmid pSLXCMV-dWF-CAT. Cells which were transfected with plasmid $pNL_{4\text{-}3}$ and with plasmid pSLXCMV-CAT expressed Vpr and CAT, and were designated WT/CAT cells. Cells which were transfected with plasmid $pNL_{4\text{-}3}$ and with plasmid pSLXCMV-VPR-CAT expressed Vpr and the Vpr-CAT chimeric protein, and were designated WT/Vpr-CAT cells. Cells which were transfected with plasmid $pNL_{4\text{-}3}$ and with plasmid pSLXCMV-dWF-CAT expressed Vpr and the dWF-CAT chimeric protein, and were designated WT/WF-CAT cells. Cells which were transfected with plasmid $pNL_{4\text{-}3DVpr}$ and with plasmid pSLXCMV-dWF-CAT did not express Vpr, expressed the dWF-CAT chimeric protein, and were designated $Vpr^-$/WF-CAT cells.

The ability of each type of cells to generate HIV-1 virions was confirmed by sucrose gradient centrifugation analysis, as described herein and depicted in FIGS. 10A–10D. The amount of CAT activity present in cell extracts prepared from cells of each type was assessed. The amount of CAT activity present in virions generated by cells of each type was also assessed. These results are shown in FIG. 11.

Figure 11:
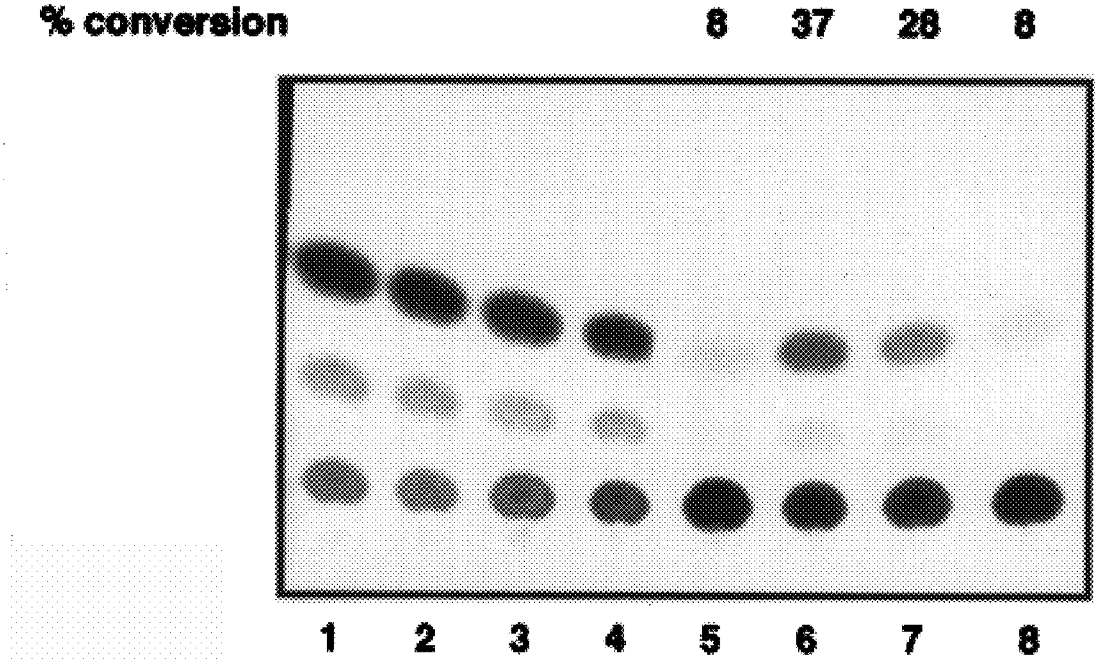
FIG. 11 is an image of a thin-layer chromatograph prepared to assess CAT activity in centrifugal sedimentation fractions prepared using extracts from cells designated WT/CAT, WT/Vpr-CAT, WT/WF-CAT, or $Vpr^-$/WF-CAT cells. CAT activity was assessed in the cell extract of a cell culture (lanes 1–4) or in HIV-1 virions collected from the cell culture supernatant of a cell culture (lanes 5–8). Cells and virions, respectively, obtained from WT/CAT cell culture were used in the assay mixtures applied to lanes 1 and 5. Cells and virions, respectively, obtained from WT/Vpr-CAT cell culture were used in the assay mixtures applied to lanes 2 and 6. Cells and virions, respectively, obtained from WT/dWF-CAT cell culture were used in the assay mixtures applied to lanes 3 and 7. Cells and virions, respectively, obtained from $Vpr^-$/dWF-CAT cell culture were used in the assay mixtures applied to lanes 4 and 8.

As indicated by lanes 7 and 8 of FIG. 11, virions which were generated by WT/WF-CAT cells exhibited significantly higher CAT activity (28% conversion of chloramphenicol to an acetylated product) than virions which were generated by $Vpr^-$/WF-CAT cells (8% conversion). As expected, CAT activity was also exhibited by virions which were generated by WT/Vpr-CAT cells (37% conversion; lane 6 of FIG. 11), which expressed the Vpr-CAT chimeric protein. CAT activity exhibited by virions which were generated by $Vpr^-$/WF-CAT cells was comparable to CAT activity exhibited by virions which were generated by WT/CAT cells (each 8% conversion; lanes 5 and 8, respectively, of FIG. 11). Cell extracts obtained from each of the four types of cells exhibited similar CAT activity, as shown in lanes 1 to 4 of FIG. 11.

These results indicate that Vpr interacts with a polypeptide region having an amino acid sequence comprising SEQ ID NO: 1. By engineering this motif into the amino acid sequence of a polypeptide, one can induce delivery of the engineered polypeptide into HIV-1 virions.

Other Observations.

An amino acid sequence comprising the Trp-Xaa-Xaa-Phe (SEQ ID NO: 31) motif was identified in the amino terminal domain of TFIIB, a protein known to capable of interacting with Vpr. Preliminary data indicate that isoforms of TFIIB in which an amino acid residue of the Trp-Xaa-Xaa-Phe (SEQ ID NO: 31) motif is replaced by a different amino acid residue are unable to interact with Vpr.

It has been reported that the cellular DNA repair protein designated HH23A interacts with Vpr, although the interaction occurs with a binding affinity less than the binding affinity between Vpr and other proteins, such as UDG (Withers-Ward et al., 1997, J. Virol. 71:9732–9742). The amino acid sequence of a carboxyl terminal region of HH23A comprises a region of four amino acid residues which exhibit the motif Phe-Xaa-Xaa-Phe (SEQ ID NO: 32). This motif is conserved among the HH23A proteins of various species. The ability of Vpr to interact with HH23A indicates that if the Trp residue of the Trp-Xaa-Xaa-Phe (SEQ ID NO: 31) motif described herein is replaced by a Phe residue, the presence of the motif in the amino acid sequence of a protein renders the protein capable of interacting with Vpr, albeit with a binding affinity lower than the binding affinity of Vpr and a protein having an amino acid sequence comprising the Trp-Xaa-Xaa-Phe (SEQ ID NO: 31) motif. Thus, the Phe-Xaa-Xaa-Phe (SEQ ID NO: 32) motif may be used in place of the Trp-Xaa-Xaa-Phe (SEQ ID NO: 31) motif in the compositions and methods of the invention.

EXAMPLE 2

Fusion of a Vpr Interactor Peptide to Integrase Restores Integration Activity to Integrase-Defective HIV-1 Virions The experiments presented in this Example demonstrate that fusion of a Vpr region to a protein which does not normally comprise such a region renders the protein susceptible to uptake into a retrovirus virion. In these experiments, a chimeric protein was made by fusing a 23-amino acid portion (SEQ ID NO: 1) to the amino terminus of human immunodeficiency virus-1 integrase (HIV-1 IN). Expression of this protein in cells infected with IN-defective HIV-1 virions resulted in production of progeny virions which comprised IN and which were integration-competent. Thus, the experiments presented in this Example demonstrate the operability of the compositions and methods of the invention.

The materials and methods used in the experiments presented in this Example are now described.

The HIV-1 molecular clones used included $pNL_{4\text{-}3}$ and $pNL_{1\text{-}3\Delta VPR}$, obtained from the AIDS Reagent Repository, NIH, as well as HIV-1 pNL4–3, which bear the IN active site point mutation, D116N, or IN termination mutants IN (1–4) and IN(1-234). These clones have been described (e.g. Engelman et al., 1995, J. Virol. 69:2729–2736). DNA fragments for insertion into pSLX-CMV-Vpr and pSLX-CMV-dWF expression vectors were amplified by PCR from the bacterial expression plasmid, pKK223-NY5-IN (Parke-Davis Pharmaceuticals Inc) using Vent polymerase (New England Biolabs, Beverly, Mass.). The use of the IN expression cassette from pKK223-NY5-IN was important because the DNA sequences that encode IN differ significantly from the wild type, and are unable to recombine with the provirus-encoded DNA sequence.

The 5' primers for the amplification reactions contained a unique MluI site followed by sequences in-frame for IN or PR-IN. PR-IN incorporates sequences in the primer to append an additional 10 amino acids upstream of IN that add the natural HIV-1 protease cleavage site at the junction between RNase H and IN. The sequences of the forward primers were 5'-GCGCAAGCTT CGTTCCTGGA CGGTATCGAT-3' (which lacks the protease cleavage site; SEQ ID NO: 53) and 5'-CCCACGCGTT TGGTCAGTGC TGGAATCAGG AAAGTACTAT TCCTGGACGG T-3' (comprising the protease cleavage site; SEQ ID NO: 54). The common 3' primer used for amplification of all inserts was anchored upon terminal IN sequences followed by a BglII site for insertion into the SLX-CMV vector, the sequence of which was 5'-GGCAGATCTA AGCTTTAGCT TCGTCCTG-3'. All plasmids were sequenced through the inserts for their integrity prior to use.

Cell Transfection and Infection:

Using the calcium phosphate method for delivery of DNA into cells (Profection™, Promega Corp., Madison, Wis.), cells of human kidney carcinoma cell line 293T were transfected using HIV-1 proviral clones or co-transfected with these templates and SLX-CMV-VPR-IN, SLX-CMV-VPR-PR-IN, SLX-CMV-WF-IN, or SLX-CMV-dWF-PR-IN. Three days post-transfection, cell supernatants containing virus were harvested and clarified by low-speed centrifugation. HeLa-CD4-LTR/β-gal cells grown in either 60×14 or 35×10 millimeter plates were infected in duplicate at about 10–15% confluence using various viral stocks. Addition of supernatant to these MAGI reporter cells was adjusted, based upon HIV-1 p24 antigen content as quantitated by ELISA analysis (Kimpton et al., 1992, J. Virol. 66:2232–2239). MAGI cells contain an integrated cassette comprising the β-galactoside gene (β-gal) under the control of the HIV-1 long terminal repeat, and therefore can be stained for β-galactosidase activity (typically 48–72 hours post-infection).

Infected cells were fixed in a solution comprising 0.2% (v/v) glutaraldehyde and 1% (v/v) formaldehyde for 5 minutes at room temperature. Following fixation, cells were washed with phosphate buffered saline and stained using bromo-4-chloro-3-indolyl-β-D-galactopyranoside for 2 hours at 37° C. Representative fields of stained cells were photographed and numbers of deeply stained syncytia were determined either by visual counting through a microscope or from series of photographs taken in various fields of the stained cells using an Olympus CK2 microscope.

Western Blotting Analyses of Complemented HIV-1 Virions 293T cells were grown in duplicate 100×20 millimeter culture dishes and transfected as described in the previous section. Virions released into the cell culture medium 2 ½ to 3 days post-transfection were centrifuged at 2000 rpm for 5 minutes at 4° C. to remove cellular debris. Afterward, virions were concentrated by adding 10 milliliters of cell medium atop 2 milliliters of buffered, isotonic 20% (w/v) sucrose, and ultracentrifuging the cushioned medium at 40,000 rpm for 2 hours. The bulk of the solution was removed by careful pipetting, and pelleted virions (visible as slight white pellets) were removed from the bottom of the ultracentrifuge tubes by resuspension in residual medium, typically resulting in a volume of 60 to 100 microliters of concentrated virus particles.

Particles were loaded into 10–20% (w/v) Tris-HCl or Tris-tricine precast gradient gels (Bio-Rad Laboratories, Richmond, Calif.) and electrophoresed until the bromphenyl blue marker migrated to at least the bottom of the gel. Proteins were transferred from the gel to a Polyscreen transfer membrane using a semidry transfer apparatus as recommended by NEN Life Science Products. IN or IN chimera proteins were detected using a rabbit anti-IN polyclonal serum and visualized by chemiluminescence development (NEN Life Science Products) of bound HRP-conjugated anti-rabbit 1gG antisera used at 1/1500 dilution (Sigma Chemical Co., St. Louis, Mo.).

The results of the experiments presented in this Example are now described.

These experiments were conducted in order to confirm that the presence of a Vpr binding region of the invention (e.g. SEQ ID NO: 30) in a protein directs incorporation of the protein into HIV-1 virions. The protein used in these experiments was a fusion protein comprising an HIV-1 IN having a 23-amino acid Vpr binding region (SEQ ID NO: 1) fused to the amino terminus thereof. IN-defective HIV-1 virus constructs were used to detect incorporation of IN therein (i.e. by detecting restoration of IN function in progeny virions).

HIV-1 proviral expression plasmids which were used comprised pol genes in which the D,D(35)E domain was either altered or missing. This domain is known to be necessary for uptake of IN into progeny HIV-1 virions. Thus, expression of these plasmids in the absence of the fusion protein of this Example resulted in formation of HIV-1 virions which lacked IN activity, and were therefore unable to integrate into the genomes of cells infected thereby.

Figures 12A, 12C:
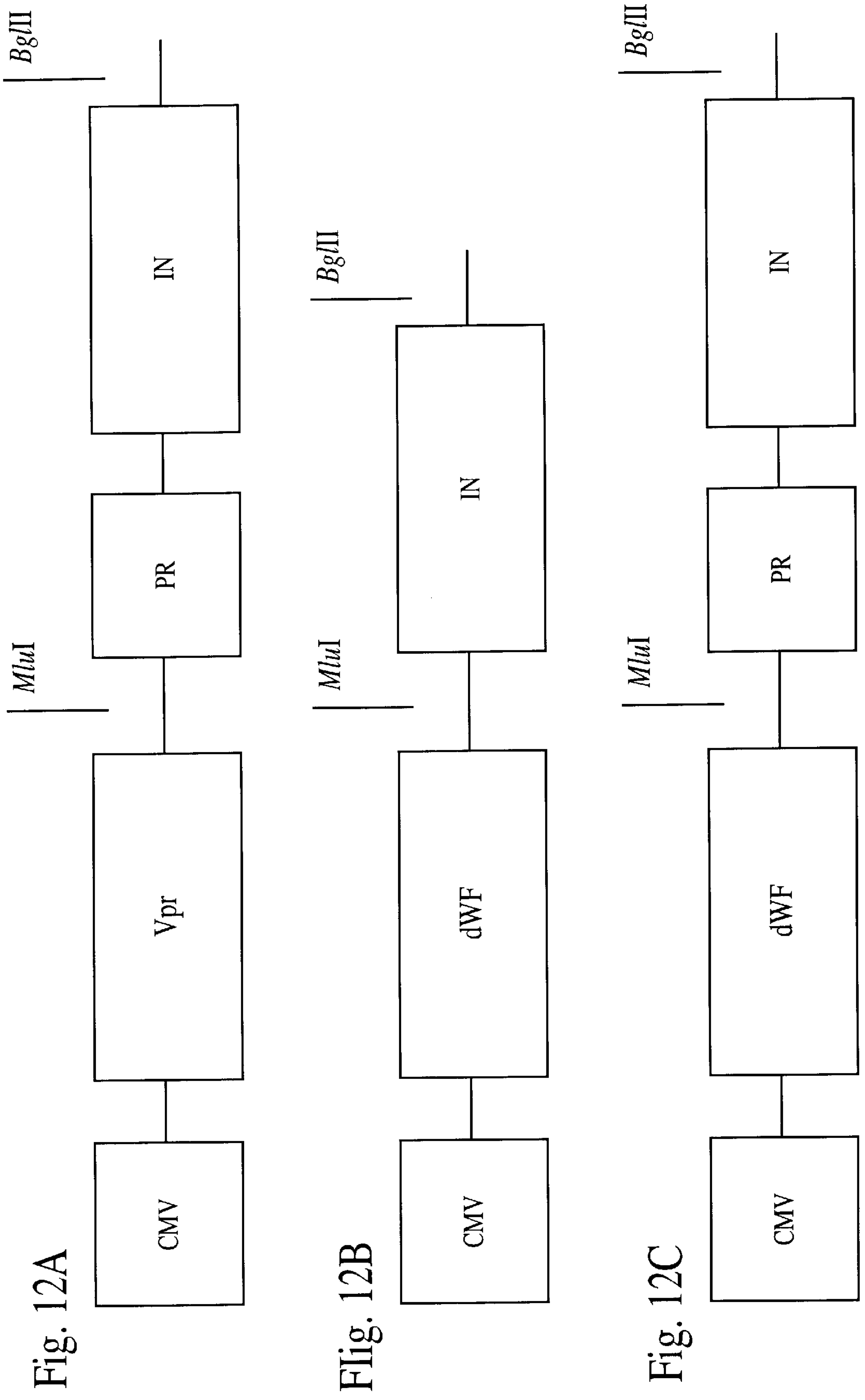

Plasmid constructs used to express the fusion protein of the Example are depicted in FIGS. 12A, 12B, and 12C.

IN activity was detected using the syncytia formation assay described in this Example. The results of this assay are listed in Table 4.

TABLE 4

Syncytia Formation in 293T Cells Infected with IN-Defective HIV-1 Particles Complemented with VPR-PR-IN, dWF-IN, or dWF-PR-IN

| HIV-1 Provirus Template | IN Chimera | Number of Syncytia Formed[B] | % of Wild Type |
|---|---|---|---|
| Wild Type[A] | none | 202 | 100.0 |
| D116N | none | 14 | 6.8[C] |
| D116N | dWF-IN | 42 | 20.8 |
| D116N | dWF-PR-IN | 52 | 25.7 |
| D116N | Vpr-PR-IN | 43 | 21.3 |
| IN (1–234) | none | 13 | 6.4[C] |
| IN (1–234) | dWF-PR-IN | 44 | 21.7 |

Note:
[A]Wild type NL4-3 provirus template (not IN-defective)
[B]Average values obtained from duplicate experiments
[C]It is believed that these values represent "background" staining using the procedure described herein, and are not representative of syncytia formation, but rather likely represent division of a singly stained cell yielding a four-cell figure.

The data listed in Table 4 indicate that expression of any one these three fusion proteins in trans with infection of producer cells with IN-defective virions yielded integration-competent progeny virions at an efficiency (i.e. number of integration-competent progeny virions/total number of progeny virions) approximately 20–25% that of wild type HIV-1. This efficiency is consistent with the efficiency of integration-competent progeny virion production effected by fusing Vpr protein directly to IN (Liu et al., 1997, J. Virol. 71:7704–7710; Fletcher et al., 1997, EMBO J. 16:5123–5138).

The three fusion protein expression plasmids designated pSLX-CMV-VPR-PR-IN, pSLX-CMV-dWF-IN, and pSLX-CMV-dWF-PR-IN complemented IN mutants IN(D116N), IN(1-4) and IN(1-234) approximately equally well, as indicated by the data listed in Table 5.

TABLE 5

Syncytia Formation in 293T Cells Infected with IN-Defective HIV-1 Particles Complemented with VPR-PR-IN, dWF-IN, or dWF-PR-IN

| HIV-1 Provirus Template | IN Chimera | Number of Syncytia Formed |
|---|---|---|
| IN (1–4) | none | 2 |
| IN (1–4) | dWF-IN | 10 |
| IN (1–4) | dWF-PR-IN | 18 |
| IN (1–4) | Vpr-PR-IN | 16 |
| IN (1–234) | none | 3 |
| IN (1–234) | dWF-IN | 14 |
| IN (1–234) | dWF-PR-IN | 20 |
| IN (1–234) | Vpr-PR-IN | 18 |

The presence of the fusion protein in progeny virions was demonstrated by Western blotting. Furthermore, the presence of dWF-fusion proteins in progeny virions was dependent on expression of Vpr in cells in which the progeny virions were produced. The copy number of the fusion protein imported into progeny virions was dependent upon the ratio of producer cell transfection using the chimera expression plasmid to producer cell transfection using the proviral clone.

The rate of syncytia formation in 293T cells appeared to be proportional to the level of IN fusion protein in progeny virions. Furthermore, the amount of dWF-IN fusion protein incorporated into integration-competent progeny virion appeared to be equal to the amount of IN(D116N) protein incorporated into progeny virions produced therefrom, indicating that dWF-IN fusion protein is incorporated into HIV-1 virions in amounts equal to IN in wild type HIV-1 virions.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of rendering a polypeptide capable of binding with Vpr, the method comprising altering the polypeptide such that the altered polypeptide comprises a Vpr-binding region having the amino acid sequence Phe-$Xaa_2$-$Xaa_3$-Phe (SEQ ID NO: 32)

wherein each of $Xaa_2$ and $Xaa_3$ is any amino acid residue, wherein the polypeptide does not normally comprise the region, and wherein the alteration does not comprise fusing the polypeptide with Vpr, whereby the altered polypeptide is capable of binding with Vpr.

2. A method of rendering a polypeptide susceptible to incorporation into a virion of a virus which normally expresses Vpr, the method comprising altering the polypeptide such that the altered polypeptide comprises a Vpr-binding region having the amino acid sequence Phe-$Xaa_2$-$Xaa_3$-Phe (SEQ ID NO: 32)

wherein each of $Xaa_2$ and $Xaa_3$ is any amino acid residue, wherein the polypeptide does not normally comprise the region, and wherein the alteration does not comprise fusing the polypeptide with Vpr, whereby the altered polypeptide is susceptible to incorporation into the virion.

* * * * *

SEQUENCE LISTING

```
<160> NUMBER OF SEQ ID NOS: 58

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence:d-WF Amino
      Acid Sequence

<400> SEQUENCE: 1

Met Gln Pro Trp Trp Ala Phe Phe Gly Gly Gly Ser Ser Trp Trp Ser
  1               5                  10                  15

Phe Ser Met Gly Pro Thr Arg
             20


<210> SEQ ID NO 2
<211> LENGTH: 76
<212> TYPE: DNA
<213> ORGANISM: Artificial Sequence
<220> FEATURE:
<223> OTHER INFORMATION: Description of Artificial Sequence:d-WF
      Oligonucleotide

<400> SEQUENCE: 2

ggatccatgg cagccttggt gggctttttt tggcggcggg agcagttggt ggtctttttc      60

gatggggccc acgcgt                                                      76


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:Vpr-
      Specific Polypeptide Binding Region

<400> SEQUENCE: 3

Gln Pro Trp Trp Ala Phe Phe
  1               5
```

-continued

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 4

Thr Pro Trp Trp Ser Phe Met
1 5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 5

Ser Trp Trp Ser Phe Tyr Pro
1 5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 6

Ser Trp Trp Ser Phe Ser Met
1 5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 7

Ala Trp Trp Glu Phe Leu Asp
1 5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 8

Lys Trp Trp Glu Phe Pro Ala
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region -continued

<400> SEQUENCE: 9

Thr Trp Trp His Phe Pro Ala
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 10

Gln Asn Trp Trp Phe Ser Phe
1 5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 11

Thr Thr Trp Trp Trp Gln Phe
1 5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 12

Ser Ala Pro Trp Trp Thr Phe
1 5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 13

Leu Pro Pro Trp Ala Ala Phe
1 5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:Vpr-Specific Polypeptide Binding Region

<400> SEQUENCE: 14

Gly His Thr Trp Trp Thr Phe
1 5

<210> SEQ ID NO 15
<211> LENGTH: 7
<212> TYPE: PRT

-continued

<213> ORGANISM: Artificial Sequence
<220> FEATURE:
<223> OTHER INFORMATION: Description of Artificial Sequence:Vpr-Specific
Polypeptide Binding Region

<400> SEQUENCE: 15

Lys Pro Met Trp Trp His Phe
1 5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:Vpr-Specific
Polypeptide Binding Region

<400> SEQUENCE: 16

Ser Trp Trp Ser Phe Thr Pro
1 5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:Vpr-Specific
Polypeptide Binding Region

<400> SEQUENCE: 17

Trp His Ser Phe Pro Pro Pro
1 5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
Vpr-Specific Polypeptide Binding Region

<400> SEQUENCE: 18

Trp His Ser Phe Pro Asp Ser
1 5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:
Vpr-Specific Polypeptide Binding Region

<400> SEQUENCE: 19

Trp His Asp Phe Pro Leu Val
1 5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence:
Vpr-Specific Polypeptide Binding Region

<400> SEQUENCE: 20

Gly Trp Tyr Ala Phe Thr Gln
1 5

-continued

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:
Vpr-Specific Polypeptide Binding Region

<400> SEQUENCE: 21

Ser Trp Trp Asp Phe Gln Asn
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence:
Vpr-Specific Polypeptide Binding Region

<400> SEQUENCE: 22

Trp His Thr Phe Asp Tyr Ser
1 5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region

<400> SEQUENCE: 23

Lys Pro Lys Trp Ala Ile Val
1 5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region

<400> SEQUENCE: 24

Thr Pro Thr Leu Glu Ala Ala
1 5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region

<400> SEQUENCE: 25

Ser Pro Leu Asn Thr Gln Arg
1 5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region -continued

<400> SEQUENCE: 26

Thr His Leu Ser Phe Leu Ser
1 5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region

<400> SEQUENCE: 27

Tyr His Ser Phe Asn Gly Thr
1 5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region

<400> SEQUENCE: 28

Ser Pro Pro Ser Ala Met Leu
1 5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:
Vpr-specific polypeptide binding region

<400> SEQUENCE: 29

Trp His Asp Trp Ala Tyr Trp
1 5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:Vpr-binding
region
<220> FEATURE:
<221> NAME/KEY: SITE
<222> LOCATION: (1)
<223> OTHER INFORMATION: Xaa is either Trp or Phe
<220> FEATURE:
<221> NAME/KEY: SITE
<222> LOCATION: (1)
<223> OTHER INFORMATION: Xaa is preferably Trp
<220> FEATURE:
<221> NAME/KEY: SITE
<222> LOCATION: (2)
<223> OTHER INFORMATION: Xaa is any amino acid residue
<220> FEATURE:
<221> NAME/KEY: SITE
<222> LOCATION: (2)
<223> OTHER INFORMATION: Xaa is preferably Ala, Trp, His, Phe, or Try
<220> FEATURE:
<221> NAME/KEY: SITE
<222> LOCATION: (2)
<223> OTHER INFORMATION: Xaa is more preferably Trp
<220> FEATURE:
<221> NAME/KEY: SITE
<222> LOCATION: (3)

-continued

<223> OTHER INFORMATION: Xaa is any amino acid residue
<220> FEATURE:
<221> NAME/KEY: SITE
<222> LOCATION: (3)
<223> OTHER INFORMATION: Xaa is preferably Gln, Thr, Ala, His, Ser, Asp, Glu, or Phe

<400> SEQUENCE: 30

Xaa Xaa Xaa Phe
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:Vpr-binding region
<220> FEATURE:
<221> NAME/KEY: SITE
<222> LOCATION: (2)
<223> OTHER INFORMATION: Xaa is any amino acid residue
<220> FEATURE:
<221> NAME/KEY: SITE
<222> LOCATION: (2)
<223> OTHER INFORMATION: Xaa is preferably Ala, Trp, His, Phe, or Tyr
<220> FEATURE:
<221> NAME/KEY: SITE
<222> LOCATION: (2)
<223> OTHER INFORMATION: Xaa is more preferably Trp
<220> FEATURE:
<221> NAME/KEY: SITE
<222> LOCATION: (3)
<223> OTHER INFORMATION: Xaa is any amino acid residue
<220> FEATURE:
<221> NAME/KEY: SITE
<222> LOCATION: (3)
<223> OTHER INFORMATION: Xaa is preferably Gln, Thr, Ala, His, Ser, Asp, Glu, or Phe

<400> SEQUENCE: 31

Trp Xaa Xaa Phe
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:Vpr-binding region
<220> FEATURE:
<221> NAME/KEY: SITE
<222> LOCATION: (2)
<223> OTHER INFORMATION: Xaa is any amino acid residue
<220> FEATURE:
<221> NAME/KEY: SITE
<222> LOCATION: (2)
<223> OTHER INFORMATION: Xaa is preferably Ala, Trp, His, Phe, or Tyr
<220> FEATURE:
<221> NAME/KEY: SITE
<222> LOCATION: (2)
<223> OTHER INFORMATION: Xaa is more preferably Trp
<220> FEATURE:
<221> NAME/KEY: SITE
<222> LOCATION: (3)
<223> OTHER INFORMATION: Xaa is any amino acid residue
<220> FEATURE:
<221> NAME/KEY: SITE
<222> LOCATION: (3)
<223> OTHER INFORMATION: Xaa is preferably Gln, Thr, Ala, His, Ser, Asp, Glu, or Phe

<400> SEQUENCE: 32

-continued

Phe Xaa Xaa Phe
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Linker region interposed between two Vpr rgions

<400> SEQUENCE: 33

Gly Gly Gly Cys
1

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Protein segment comprising two Vpr regions
<220> FEATURE:
<221> NAME/KEY: SITE
<222> LOCATION: (2)
<223> OTHER INFORMATION: Xaa is any amino acid residue
<220> FEATURE:
<221> NAME/KEY: SITE
<222> LOCATION: (2)
<223> OTHER INFORMATION: Xaa is preferabaly Ala, Trp, His, Phe, or Tyr
<220> FEATURE:
<221> NAME/KEY: SITE
<222> LOCATION: (2)
<223> OTHER INFORMATION: Xaa is more preferably Trp
<220> FEATURE:
<221> NAME/KEY: SITE
<222> LOCATION: (3)
<223> OTHER INFORMATION: Xaa is any amino acid residue
<220> FEATURE:
<221> NAME/KEY: SITE
<222> LOCATION: (3)
<223> OTHER INFORMATION: Xaa is preferably Gln, Thr, Ala, His, Ser, Asp, Glu or Phe
<220> FEATURE:
<221> NAME/KEY: SITE
<222> LOCATION: (10)
<223> OTHER INFORMATION: Xaa is any amino acid residue
<220> FEATURE:
<221> NAME/KEY: SITE
<222> LOCATION: (10)
<223> OTHER INFORMATION: Xaa is preferably Ala, Trp, His, Phe, or Tyr
<220> FEATURE:
<221> NAME/KEY: SITE
<222> LOCATION: (10)
<223> OTHER INFORMATION: Xaa is more preferably Trp
<220> FEATURE:
<221> NAME/KEY: SITE
<222> LOCATION: (11)
<223> OTHER INFORMATION: Xaa is any amino acid residue
<220> FEATURE:
<221> NAME/KEY: SITE
<222> LOCATION: (11)
<223> OTHER INFORMATION: Xaa is preferably Gln, Thr, Ala, His, Ser, Asp, Glu, or Phe

<400> SEQUENCE: 34

```
Trp Xaa Xaa Phe Gly Gly Gly Cys Trp Xaa Xaa Phe
  1               5                  10
```

<210> SEQ ID NO 35
<211> LENGTH: 76
<212> TYPE: DNA
<213> ORGANISM: Artificial Sequence
<220> FEATURE:

-continued

<223> OTHER INFORMATION: Description of Artificial Sequence:WF-dimer 1

<400> SEQUENCE: 35
cggatccatg cagccttggt gggctttttt tggcggcggg agcagttggt ggtctttttc 60
gatggggccc acgcgt 76

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence:WF-dimer 2

<400> SEQUENCE: 36
acgcgtgggc cccatcgaaa aagaccacca actgctcccg ccgc 44

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: 5' Primer UDG1

<400> SEQUENCE: 37
aaagaattcc cctcctcgcc gctgagtgcc 30

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: 3' Primer UDG2

<400> SEQUENCE: 38
cccattgact ggaaggagct gtgagtcgac taaatc 36

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Mutated Complementary Primer of Pair UDG222

<400> SEQUENCE: 39
gagcgaggcg gggagcagtt c 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Mutated Complementary Primer of Pair UDG222

<400> SEQUENCE: 40
gaactgctcc ccgcctcggt c 21

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Mutated -continued Complementary Primer of Pair UDG225

<400> SEQUENCE: 41
ggctgggagc agggcactgt gcagtt 26

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Mutated
Complementary Primer of Pair UDG225

<400> SEQUENCE: 42
aactgcatca gtgccctgct cccagcc 27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Mutated
Complementary Primer of Pair UDG152

<400> SEQUENCE: 43
catggaccta atctagctca cgggctc 27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Mutated
Complementary Primer of Pair UDG152

<400> SEQUENCE: 44
gagcccgtga gctagattag gtccatg 27

<210> SEQ ID NO 45
<211> LENGTH: 4
<212> TYPE: PRT
<213> ORGANISM: Homo sapiens
<220> FEATURE:
<223> OTHER INFORMATION: Amino Acid Residues 222-225 of Human UDG

<400> SEQUENCE: 45

Trp Glu Gln Phe
1

<210> SEQ ID NO 46
<211> LENGTH: 29
<212> TYPE: PRT
<213> ORGANISM: Homo sapiens
<220> FEATURE:
<223> OTHER INFORMATION: Amino Acid Residues 210-238 of Human UDG

<400> SEQUENCE: 46

Arg Ala His Gln Ala Asn Ser His Lys Glu Arg Gly Trp Glu Gln Phe
1 5 10 15

Thr Asp Ala Val Val Ser Trp Leu Asn Gln Asn Ser Asn
20 25

<210> SEQ ID NO 47
<211> LENGTH: 29
<212> TYPE: PRT
<213> ORGANISM: Saccharomyces cerevisiae -continued

```
<220> FEATURE:
<223> OTHER INFORMATION: Amino Acid Residues 228-256 of Yeast UDG

<400> SEQUENCE: 47

Arg Ala His Asn Ala Asn Ser Glu Ser Lys His Gly Trp Glu Thr Phe
  1               5                  10                  15

Thr Lys Arg Val Val Gln Leu Leu Ile Gln Asp Arg Glu
             20                  25


<210> SEQ ID NO 48
<211> LENGTH: 29
<212> TYPE: PRT
<213> ORGANISM: Escherichia coli
<220> FEATURE:
<223> OTHER INFORMATION: Amino Acid Residues 129-157 of E. coli UDG

<400> SEQUENCE: 48

Arg Ala Gly Gln Ala His Ser Glu Ala Ser Leu Gly Trp Glu Thr Phe
  1               5                  10                  15

Thr Asp Lys Val Ile Ser Leu Ile Asn Gln His Arg Glu
             20                  25


<210> SEQ ID NO 49
<211> LENGTH: 29
<212> TYPE: PRT
<213> ORGANISM: Herpes Simplex Virus 1
<220> FEATURE:
<223> OTHER INFORMATION: Amino Acid Residues 243-271 of HSV-1 UDG

<400> SEQUENCE: 49

Lys Arg Gly Ala Ala Ala Ser Glu Ser Arg Ile Gly Trp Asp Arg Phe
  1               5                  10                  15

Val Gly Gly Val Ile Arg Arg Leu Ala Ala Arg Arg Pro
             20                  25


<210> SEQ ID NO 50
<211> LENGTH: 29
<212> TYPE: PRT
<213> ORGANISM: Herpes Simplex Virus 2
<220> FEATURE:
<223> OTHER INFORMATION: Amino Acid Residues 223-251 of HSV-2 UDG

<400> SEQUENCE: 50

Lys Arg Gly Ala Ala Ala Ser Thr Ser Lys Leu Gly Trp Asp Arg Phe
  1               5                  10                  15

Val Gly Gly Val Val Arg Arg Leu Ala Ala Arg Arg Pro
             20                  25


<210> SEQ ID NO 51
<211> LENGTH: 29
<212> TYPE: PRT
<213> ORGANISM: Epstein-Barr Virus
<220> FEATURE:
<223> OTHER INFORMATION: Amino Acid Residues 155-183 of EBV UDG

<400> SEQUENCE: 51

Gln Lys Gly Lys Pro Gly Ser Glu Ala Asp Ile Gly Trp Ala Trp Phe
  1               5                  10                  15

Thr Asp His Val Ile Ser Leu Leu Ser Glu Arg Leu Lys
             20                  25


<210> SEQ ID NO 52
<211> LENGTH: 4
<212> TYPE: PRT
```

-continued

```
<213> ORGANISM: Artificial Sequence
<220> FEATURE:
<223> OTHER INFORMATION: Description of Artificial Sequence: dWF-CAT
      Chimeric Protein Linker Sequence

<400> SEQUENCE: 52

Gly Gly Gly Ser
  1


<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence:
      Amplification Primer

<400> SEQUENCE: 53

gcgcaagctt cgttcctgga cggtatcgat                                        30


<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence:
      Amplification Primer

<400> SEQUENCE: 54

cccacgcgtt tggtcagtgc tggaatcagg aaagtactat tcctggacgg t                51


<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence:
      Amplification Primer

<400> SEQUENCE: 55

ggcagatcta agctttagct tcgtcctg                                          28


<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: 96gIII
      Sequencing Primer

<400> SEQUENCE: 56

ccctcatagt tagcgtaacg                                                   20


<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: PCR Primer
      Vpr-1

<400> SEQUENCE: 57

cggatccatg gaacaagccc cagaagac                                          28


<210> SEQ ID NO 58
<211> LENGTH: 25
<212> TYPE: DNA
```

-continued

```
<213> ORGANISM: Artificial Sequence
<220> FEATURE:
<223> OTHER INFORMATION: Description of Artificial Sequence:  PCR Primer
      Vpr-2

<400> SEQUENCE: 58

ctatagacta ggatctactg gatcc                                         25
```